United States Patent
Ido et al.

(10) Patent No.: US 10,517,928 B2
(45) Date of Patent: Dec. 31, 2019

(54) PHARMACEUTICAL COMPOSITION FOR TREATING AND/OR PREVENTING ESOPHAGEAL STENOSIS

(71) Applicant: KAGOSHIMA UNIVERSITY, Kagoshima-shi, Kagoshima (JP)

(72) Inventors: Akio Ido, Kagoshima (JP); Hirohito Tsubouchi, Kagoshima (JP); Yuga Komaki, Kagoshima (JP)

(73) Assignee: Kagoshima University, Kagoshima (JP)

( * ) Notice: Subject to any disclaimer, the term of this patent is extended or adjusted under 35 U.S.C. 154(b) by 0 days.

(21) Appl. No.: 15/503,078

(22) PCT Filed: Aug. 6, 2015

(86) PCT No.: PCT/JP2015/072385
§ 371 (c)(1),
(2) Date: Feb. 10, 2017

(87) PCT Pub. No.: WO2016/024524
PCT Pub. Date: Feb. 18, 2016

(65) Prior Publication Data
US 2017/0224773 A1    Aug. 10, 2017

(30) Foreign Application Priority Data
Aug. 12, 2014 (JP) .................... 2014-164429

(51) Int. Cl.
*A61K 38/18* (2006.01)
*A61L 31/16* (2006.01)
*A61L 31/04* (2006.01)
*A61P 1/04* (2006.01)

(52) U.S. Cl.
CPC .............. *A61K 38/18* (2013.01); *A61L 31/16* (2013.01); *A61P 1/04* (2018.01); *A61K 38/1833* (2013.01); *A61L 31/047* (2013.01); *A61L 2300/252* (2013.01); *A61L 2300/414* (2013.01)

(58) Field of Classification Search
None
See application file for complete search history.

(56) References Cited

U.S. PATENT DOCUMENTS

| | | | | | |
|---|---|---|---|---|---|
| 5,342,831 | A | * | 8/1994 | Nakamura | C07K 14/4753 435/384 |
| 6,051,557 | A | * | 4/2000 | Drucker | A61K 38/26 435/366 |
| 6,475,145 | B1 | * | 11/2002 | Baylor | A61B 5/145 600/309 |
| 2005/0255230 | A1 | * | 11/2005 | Clerc | A61L 31/10 427/2.1 |
| 2010/0330144 | A1 | | 12/2010 | Liu et al. | |
| 2012/0082706 | A1 | | 4/2012 | Nakagawa et al. | |

FOREIGN PATENT DOCUMENTS

JP    2002-345972 A    12/2002
JP    2005-168646 A     6/2005

OTHER PUBLICATIONS

Komaki et al., Gastroenterology, vol. 148, No. 4, Supplement 1, p. S-319, abstract SA-1738, Apr. 2015.*
Barret et., .PLoS One 9(7): el 00236. doi:10.1371/journal.pone.0100236, published Jul. 3, 2014.*
Tarnawski et al., Current Medical Chemistry, 19:16-27, 2012.*
International Search Report dated Oct. 6, 2015, in PCT/JP2015/072385.
Gohda et al., "Purification and Partial Characterization of Hepatocyte Growth Factor from Plasma of a Patient with Fulminant Hepatic Failure," J. Clin. Invest., Feb. 1988, 81:414-419.
Jeon et al., "Effect of drug-eluting metal stents in benign esophageal stricture: an in vivo animal study," Endoscopy, 2009, 41(5):449-456.
Makuuchi et al., "Surgical Treatment for Reflux Esophagitis," Journal of Japan Surgical Society, 2003, 104(9):582-586.
Miyazawa et al., "Molecular cloning and sequence analysis of cDNA for human hepatocyte growth factor," Biochemical and Biophysical Research Communications, 1989, 163(2):967-973.
Numata et al., "Hepatocyte Growth Factor Facilitates the Repair of Large Colonic Ulcers in 2,4,6-Trinitrobenzene Sulfonic Acid-Induced Colitis in Rats," Inflamm. Bowel Dis., Jun. 2005, 11(6):551-558.
Oki et al., "Cutting-edge esophageal regenerative medicine," Journal of Clinical and Experimental Medicine, May 22, 2010, 233(8):613-616.
Setoyama et al., "Repeated enemas with hepatocyte growth factor selectively stimulate epithelial cell proliferation of injured mucosa in rats with experimental colitis," Life Sciences, 2011, 89:269-275.
Tahara et al., "Hepatocyte Growth Factor Facilitates Colonic Mucosal Repair in Experimental Ulcerative Colitis in Rats," The Journal of Pharmacology and Experimental Therapeutics, 2003, 307(1):146-151.
Takahashi et al., "Lesion repair mechanism of tunica mucosa esophagi," G.I. Research, 1998, 6(6):430-436.

(Continued)

*Primary Examiner* — Marianne P Allen
(74) *Attorney, Agent, or Firm* — Foley & Lardner LLP

(57) ABSTRACT

According to this invention, the following are provided: a pharmaceutical composition for treating and/or preventing esophageal stenosis, comprising an HGF protein as an active ingredient (wherein the HGF protein may be a polypeptide that is any one of the following: (a) a polypeptide comprising the amino acid sequence shown in SEQ ID NO: 2; (b) a polypeptide comprising an amino acid sequence shown in SEQ ID NO: 2 in which one to several amino acids are deleted, substituted, or added; or (c) a polypeptide comprising an amino acid sequence having at least 90% identity with the amino acid sequence shown in SEQ ID NO: 2; and a stent comprising the pharmaceutical composition.

12 Claims, 8 Drawing Sheets
Specification includes a Sequence Listing.

(56) References Cited

OTHER PUBLICATIONS

Takahashi et al., "Role of hepatocyte growth factor (HGF) in the repair process of esophageal ulcer," Journal of Clinical and Experimental Medicine, Mar. 30, 1996, 176(13):852-856.
Takahashi et al., "Zoshoku Inshi kara Mita Bogyo Kiko," G.I. Research, 2002, 10(4):281-286.
Wada et al., "Enteral stent placement in the upper gastrointestinal tract: future perspectives and directions," Surgical Therapy, Jun. 2011, 104(6):875-880.
Supplementary European Search Report dated Mar. 28, 2018, in EP 15831534.1.

* cited by examiner

SEQUENCE LISTING

<160> NUMBER OF SEQ ID NOS: 22

<210> SEQ ID NO 1
<211> LENGTH: 2187
<212> TYPE: DNA
<213> ORGANISM: Homo sapiens

<400> SEQUENCE: 1

```
atgtgggtga ccaaactcct gccagccctg ctgctgcagc atgtcctcct gcatctcctc      60
ctgctcccca tcgccatccc ctatgcagag ggacaaagga aaagaagaaa tacaattcat     120
gaattcaaaa aatcagcaaa gactacccta atcaaaatag atccagcact gaagataaaa     180
accaaaaaag tgaatactgc agaccaatgt gctaatagat gtactaggaa taaaggactt     240
ccattcactt gcaaggcttt tgttttgat aaagcaagaa aacaatgcct ctggttcccc       300
ttcaatagca tgtcaagtgg agtgaaaaaa gaatttggcc atgaatttga cctctatgaa     360
aacaaagact acattagaaa ctgcatcatt ggtaaaggac gcagctacaa gggaacagta     420
tctatcacta agagtggcat caaatgtcag ccctggagtt ccatgatacc acacgaacac     480 agcttttttgc cttcgagcta tcggggtaaa gacctacagg aaaactactg tcgaaatcct     540 cgagggaag aaggggggacc ctggtgtttc acaagcaatc cagaggtacg ctacgaagtc     600
tgtgacattc ctcagtgttc agaagttgaa tgcatgacct gcaatgggga gagttatcga     660
ggtctcatgg atcatacaga atcaggcaag atttgtcagc gctgggatca tcagacacca     720
caccggcaca aattcttgcc tgaaagatat cccgacaagg gctttgatga taattattgc     780
cgcaatcccg atggccagcc gaggccatgg tgctatactc ttgaccctca cacccgctgg     840
gagtactgtg caattaaaac atgcgctgac aatactatga tgacactga tgttcctttg      900 gaaacaactg aatgcatcca aggtcaagga gaaggctaca ggggcactgt caataccatt     960
tggaatggaa ttccatgtca gcgttgggat tctcagtatc ctcacgagca tgacatgact    1020
cctgaaaatt tcaagtgcaa ggacctacga gaaaattact gccgaaatcc agatgggtct    1080
```

-continued

```
gaatcaccct ggtgttttac cactgatcca aacatccgag ttggctactg ctcccaaatt     1140
ccaaactgtg atatgtcaca tggacaagat tgttatcgtg ggaatggcaa aaattatatg     1200
ggcaacttat cccaaacaag atctggacta acatgttcaa tgtgggacaa gaacatggaa     1260
gacttacatc gtcatatctt ctgggaacca gatgcaagta agctgaatga gaattactgc     1320
cgaaatccag atgatgatgc tcatggaccc tggtgctaca cgggaaatcc actcattcct     1380
tgggattatt gccctatttc tcgttgtgaa ggtgatacca cacctacaat agtcaattta     1440
gaccatcccg taatatcttg tgccaaaacg aaacaattgc gagttgtaaa tgggattcca     1500
acacgaacaa acataggatg gatggttagt ttgagataca gaaataaaca tatctgcgga     1560
ggatcattga taaaggagag ttgggttctt actgcacgac agtgtttccc ttctcgagac     1620
ttgaaagatt atgaagcttg gcttggaatt catgatgtcc acggaagagg agatgagaaa     1680
tgcaaacagg ttctcaatgt ttcccagctg gtatatggcc ctgaaggatc agatctggtt     1740
ttaatgaagc ttgccaggcc tgctgtcctg gatgattttg ttagtacgat tgatttacct     1800
aattatggat gcacaattcc tgaaaagacc agttgcagtg tttatggctg gggctacact     1860
ggattgatca actatgatgg cctattacga gtggcacatc tctatataat gggaaatgag     1920
aaatgcagcc agcatcatcg agggaaggtg actctgaatg agtctgaaat atgtgctggg     1980
gctgaaaaga ttggatcagg accatgtgag ggggattatg gtggcccact tgtttgtgag     2040
caacataaaa tgagaatggt tcttggtgtc attgttcctg tcgtggatg tgccattcca     2100 aatcgtcctg gtattttgt ccgagtagca tattatgcaa aatggataca caaaattatt     2160
ttaacatata aggtaccaca gtcatag                                         2187
```

<210> SEQ ID NO 2
<211> LENGTH: 728
<212> TYPE: PRT
<213> ORGANISM: Homo sapiens

<400> SEQUENCE: 2

```
Met Trp Val Thr Lys Leu Leu Pro Ala Leu Leu Leu Gln His Val Leu
1               5                  10                  15

Leu His Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175
```

-continued

Cys Arg Asn Pro Arg Gly Glu Glu Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu

|  |  |  |  | 595 |  |  |  | 600 |  |  |  | 605 |  |
|---|---|---|---|---|---|---|---|---|---|---|---|---|---|
| Lys | Thr | Ser | Cys | Ser | Val | Tyr | Gly | Trp | Gly | Tyr | Thr | Gly | Leu | Ile | Asn |
|  |  |  |  | 610 |  |  |  | 615 |  |  |  | 620 |  |

Tyr Asp Gly Leu Leu Arg Val Ala His Leu Tyr Ile Met Gly Asn Glu
625                     630                     635                     640

Lys Cys Ser Gln His Arg Gly Lys Val Thr Leu Asn Glu Ser Glu
                        645                     650                     655

Ile Cys Ala Gly Ala Glu Lys Ile Gly Ser Gly Pro Cys Glu Gly Asp
                660                     665                     670

Tyr Gly Gly Pro Leu Val Cys Glu Gln His Lys Met Arg Met Val Leu
                675                     680                     685

Gly Val Ile Val Pro Gly Arg Gly Cys Ala Ile Pro Asn Arg Pro Gly
            690                     695                     700

Ile Phe Val Arg Val Ala Tyr Tyr Ala Lys Trp Ile His Lys Ile Ile
705                     710                     715                     720

Leu Thr Tyr Lys Val Pro Gln Ser
                725

<210> SEQ ID NO 3
<211> LENGTH: 2187
<212> TYPE: DNA
<213> ORGANISM: Mus musculus

<400> SEQUENCE: 3

| atgatgtggg ggaccaaact tctgccggtc ctgttgctgc agcatgtcct cctgcacctc | 60 |
| ctcctgcttc atgtcgccat ccccatgca aaggacaga agaaaagaag aaatacactt | 120 |
| catgaattta aaaagtcagc aaaaactact cttaccaagg aagacccatt actgaagatt | 180 |
| aaaaccaaaa aagtgaactc tgcagatgag tgtgccaaca ggtgtatcag gaacaggggc | 240 |
| tttacgttca cttgcaaggc cttcgttttt gataagtcaa gaaaacgatg ctactggtat | 300 |
| cctttcaata gtatgtcaag tggagtgaaa aaagggtttg ccatgaatt tgacctctat | 360 |
| gaaaacaaag actatattag aaactgcatc attggtaaag gaggcagcta taagggacg | 420 |
| gtatccatca ctaagagtgg catcaaatgc cagccttgga attccatgat cccccatgaa | 480 |
| cacagctttt tgccttcgag ctatcgcggt aaagacctac aggaaaacta ctgtcgaaat | 540 |
| cctcgagggg aagaagggg accctggtgt tcacaagca atccagaggt acgctacgaa | 600 |
| gtctgtgaca ttcctcagtg ttcagaagtt gaatgcatga cctgcaatgg tgaaagctac | 660 |
| agaggtccca tggatcacac agaatcaggc aagacttgtc agcgctggga ccagcagaca | 720 |
| ccacaccggc acaagttctt gccagaaaga tatcccgaca agggctttga tgataattat | 780 |
| tgccgcaatc ctgatggcaa gccgaggcca tggtgctaca ctcttgaccc tgacacccct | 840 |
| tgggagtatt gtgcaattaa acgtgcgct cacagtgctg tgaatgagac tgatgtccct | 900 |
| atggaaacaa ctgaatgcat tcaaggccaa ggagaaggtt acaggggaac cagcaatacc | 960 |
| atttggaatg gaattccctg tcagcgttgg gattcgcagt accctcacaa gcatgatatc | 1020 |
| actcccgaga acttcaaatg caaggacctt agagaaaatt attgccgcaa tccagatggg | 1080 |
| gctgaatcac catggtgttt taccactgac ccaaacatcc gagttggcta ctgctctcaa | 1140 |
| attcccaagt gtgacgtgtc aagtggacaa gattgttatc gtggcaatgg gaaaaattac | 1200 |
| atgggcaact atccaaaaac aaggtctgga cttacatgtt ccatgtggga caagaatatg | 1260 |
| gaggatttac accgtcatat cttctggag ccagatgcta gcaaattgaa taagaattac | 1320 |
| tgccggaatc ctgatgatga tgcccatgga ccttggtgct acacggggaa tcctctttatt | 1380 |

-continued

```
ccttgggatt attgccctat ttcccgttgt gaaggagata ctacacctac aattgtcaat    1440
ttggaccatc ctgtaatatc ctgtgccaaa acaaaacaac tgcgggttgt aaatggcatt    1500
ccaacacaaa caacagtagg gtggatggtt agtttgaaat acagaaataa acatatctgt    1560
ggaggatcat tgataaagga aagttgggtt cttactgcaa gacaatgttt tccagccaga    1620
aacaaagact tgaaagacta tgaagcttgg cttggcatcc acgatgttca tgagagaggc    1680
gaggagaagc gcaagcagat cttaaacatt tcccagctgg tctatggtcc tgaaggctca    1740
gacttggttt tactgaagct tgctcgacct gcaatcctgg ataactttgt cagtacaatt    1800
gatttaccta gttatggttg tacaatccct gaaaagacca cttgcagtat ttacggctgg    1860
ggctacactg gattgatcaa cgcggatggt ttattacgag tagctcatct gtatattatg    1920
gggaatgaga aatgcagtca gcaccatcaa ggcaaggtga ctttgaatga gtctgagtta    1980
tgtgctgggg ctgaaaagat tggatcagga ccatgtgagg gagattatgg tggcccactc    2040
atttgtgaac aacacaaaat gagaatggtt cttggtgtca ttgttcctgg tcgtggatgt    2100
gccatcccaa atcgtcctgg tattttgtt cgagtagcat attatgcaaa atggatacac    2160
aaagtaattt tgacatacaa gttgtaa                                        2187
```

<210> SEQ ID NO 4
<211> LENGTH: 728
<212> TYPE: PRT
<213> ORGANISM: Mus musculus

<400> SEQUENCE: 4

```
Met Met Trp Gly Thr Lys Leu Leu Pro Val Leu Leu Gln His Val
1               5                   10                  15

Leu Leu His Leu Leu Leu Leu His Val Ala Ile Pro Tyr Ala Glu Gly
            20                  25                  30

Gln Lys Lys Arg Arg Asn Thr Leu His Glu Phe Lys Lys Ser Ala Lys
        35                  40                  45

Thr Thr Leu Thr Lys Glu Asp Pro Leu Leu Lys Ile Lys Thr Lys Lys
    50                  55                  60

Val Asn Ser Ala Asp Glu Cys Ala Asn Arg Cys Ile Arg Asn Arg Gly
65                  70                  75                  80

Phe Thr Phe Thr Cys Lys Ala Phe Val Phe Asp Lys Ser Arg Lys Arg
                85                  90                  95

Cys Tyr Trp Tyr Pro Phe Asn Ser Met Ser Ser Gly Val Lys Lys Gly
            100                 105                 110

Phe Gly His Glu Phe Asp Leu Tyr Glu Asn Lys Asp Tyr Ile Arg Asn
        115                 120                 125

Cys Ile Ile Gly Lys Gly Gly Ser Tyr Lys Gly Thr Val Ser Ile Thr
    130                 135                 140

Lys Ser Gly Ile Lys Cys Gln Pro Trp Asn Ser Met Ile Pro His Glu
145                 150                 155                 160

His Ser Phe Leu Pro Ser Ser Tyr Arg Gly Lys Asp Leu Gln Glu Asn
                165                 170                 175

Tyr Cys Arg Asn Pro Arg Gly Glu Glu Gly Gly Pro Trp Cys Phe Thr
            180                 185                 190

Ser Asn Pro Glu Val Arg Tyr Glu Val Cys Asp Ile Pro Gln Cys Ser
        195                 200                 205

Glu Val Glu Cys Met Thr Cys Asn Gly Glu Ser Tyr Arg Gly Pro Met
    210                 215                 220
```

-continued

```
Asp His Thr Glu Ser Gly Lys Thr Cys Gln Arg Trp Asp Gln Gln Thr
225                 230                 235                 240

Pro His Arg His Lys Phe Leu Pro Glu Arg Tyr Pro Asp Lys Gly Phe
                245                 250                 255

Asp Asp Asn Tyr Cys Arg Asn Pro Asp Gly Lys Pro Arg Pro Trp Cys
            260                 265                 270

Tyr Thr Leu Asp Pro Asp Thr Pro Trp Glu Tyr Cys Ala Ile Lys Thr
        275                 280                 285

Cys Ala His Ser Ala Val Asn Glu Thr Asp Val Pro Met Glu Thr Thr
    290                 295                 300

Glu Cys Ile Gln Gly Gln Gly Glu Gly Tyr Arg Gly Thr Ser Asn Thr
305                 310                 315                 320

Ile Trp Asn Gly Ile Pro Cys Gln Arg Trp Asp Ser Gln Tyr Pro His
                325                 330                 335

Lys His Asp Ile Thr Pro Glu Asn Phe Lys Cys Lys Asp Leu Arg Glu
            340                 345                 350

Asn Tyr Cys Arg Asn Pro Asp Gly Ala Glu Ser Pro Trp Cys Phe Thr
        355                 360                 365

Thr Asp Pro Asn Ile Arg Val Gly Tyr Cys Ser Gln Ile Pro Lys Cys
    370                 375                 380

Asp Val Ser Ser Gly Gln Asp Cys Tyr Arg Gly Asn Gly Lys Asn Tyr
385                 390                 395                 400

Met Gly Asn Leu Ser Lys Thr Arg Ser Gly Leu Thr Cys Ser Met Trp
                405                 410                 415

Asp Lys Asn Met Glu Asp Leu His Arg His Ile Phe Trp Glu Pro Asp
            420                 425                 430

Ala Ser Lys Leu Asn Lys Asn Tyr Cys Arg Asn Pro Asp Asp Asp Ala
        435                 440                 445

His Gly Pro Trp Cys Tyr Thr Gly Asn Pro Leu Ile Pro Trp Asp Tyr
    450                 455                 460

Cys Pro Ile Ser Arg Cys Glu Gly Asp Thr Thr Pro Thr Ile Val Asn
465                 470                 475                 480

Leu Asp His Pro Val Ile Ser Cys Ala Lys Thr Lys Gln Leu Arg Val
                485                 490                 495

Val Asn Gly Ile Pro Thr Gln Thr Thr Val Gly Trp Met Val Ser Leu
            500                 505                 510

Lys Tyr Arg Asn Lys His Ile Cys Gly Gly Ser Leu Ile Lys Glu Ser
        515                 520                 525

Trp Val Leu Thr Ala Arg Gln Cys Phe Pro Ala Arg Asn Lys Asp Leu
    530                 535                 540

Lys Asp Tyr Glu Ala Trp Leu Gly Ile His Asp Val His Glu Arg Gly
545                 550                 555                 560

Glu Glu Lys Arg Lys Gln Ile Leu Asn Ile Ser Gln Leu Val Tyr Gly
                565                 570                 575

Pro Glu Gly Ser Asp Leu Val Leu Leu Lys Leu Ala Arg Pro Ala Ile
            580                 585                 590

Leu Asp Asn Phe Val Ser Thr Ile Asp Leu Pro Ser Tyr Gly Cys Thr
        595                 600                 605

Ile Pro Glu Lys Thr Thr Cys Ser Ile Tyr Gly Trp Gly Tyr Thr Gly
    610                 615                 620

Leu Ile Asn Ala Asp Gly Leu Leu Arg Val Ala His Leu Tyr Ile Met
625                 630                 635                 640

Gly Asn Glu Lys Cys Ser Gln His His Gln Gly Lys Val Thr Leu Asn
```

|  |  | 645 |  |  | 650 |  |  | 655 |  |
|--|--|--|--|--|--|--|--|--|--|

Glu Ser Glu Leu Cys Ala Gly Ala Glu Lys Ile Gly Ser Gly Pro Cys
          660                665                670

Glu Gly Asp Tyr Gly Gly Pro Leu Ile Cys Glu Gln His Lys Met Arg
        675                  680                685

Met Val Leu Gly Val Ile Val Pro Gly Arg Gly Cys Ala Ile Pro Asn
      690                  695                700

Arg Pro Gly Ile Phe Val Arg Val Ala Tyr Tyr Ala Lys Trp Ile His
705                710                715              720

Lys Val Ile Leu Thr Tyr Lys Leu
        725

<210> SEQ ID NO 5
<211> LENGTH: 2187
<212> TYPE: DNA
<213> ORGANISM: Rattus norvegicus

<400> SEQUENCE: 5

```
atgatgtggg ggaccaaact tctgccggtc ctgttgctgc agcatgtcct gctgcacctc    60
ctcctgcttc ctgtcaccat ccctatgca aaggacaga agaagagaag aaatactctt   120
catgaattca aaaagtcagc aaaaactact cttaccaagg aagacccatt agtgaagatt   180
aaaaccaaaa agtgaactc tgcagatgag tgtgccaaca ggtgcatcag aaacaagggc   240
tttccattca cttgcaaggc cttttgttttt gataagtcga gaaaacgatg ctactggtat   300
cctttcaata gtatgtcaag tggagtgaaa aaagggtttg ccatgaatt tgacctctat   360
gaaaacaaag actatattag aaattgcatc attggtaaag gaggcagcta aagggggaca   420
gtatccatca ctaagagtgg catcaagtgc cagccttgga attccatgat cccccatgaa   480
cacagctttt tgccttcgag ctatcgcggt aaagacctac aggaaaacta ctgtcgaaat   540
cctcgagggg aagaagggg accctggtgt tcacaagca atccagaggt acgctacgaa   600
gtctgtgaca ttcctcagtg ttcagaagtt gaatgcatga cctgcaacgg tgaaagctac   660
agaggtccca tggatcacac agaatcaggc aagacatgtc agcgctggga tcagcagaca   720
ccacaccggc acaaattctt gccggaaaga tatcccgaca agggctttga tgataattat   780
tgccgcaatc ccgatggcaa gccgaggcca tggtgctaca ctcttgaccc tgacacccct   840
tgggagtatt gtgcaattaa aatgtgcgct cacagtgctg tgaatgagac tgatgttccc   900
atggaaacaa ctgaatgtat aaaaggccaa ggagaaggtt acaggggaac caccaatacc   960
atttggaatg gaattccgtg tcagcgttgg gattcgcagt accccacaa gcatgacatc  1020
actcccgaga acttcaaatg caaggacctt agagaaaatt attgccgcaa tccggatggg  1080
gctgaatcac catggtgttt taccactgat ccaaacatcc gagttggtta ctgctctcaa  1140
attcccaaat gtgacgtgtc aagtggacaa gattgttatc gtggcaatgg gaaaaactac  1200
atgggcaact tatccaaaac aaggtctgga ctcacatgtt ccatgtggga caagaatatg  1260
gaggatttac accgtcatat cttctgggag ccagacgcta gcaagttgac taagaattac  1320
tgccggaacc ccgatgacga cgcccatgga ccttggtgct acacagggaa tcctctcgtt  1380
ccttgggatt attgccctat ttcccgttgt gaaggagata ctacacctac aattgtcaat  1440
ttggaccatc ctgtaatatc ctgtgccaaa acaaacaac tgcgagttgt aaatggcatt  1500
ccaacacaaa caacagtagg gtggatggtt agtttgaaat acaggaataa acacatctgt  1560
gggggatcat tgataaagga agttgggtt cttactgcaa ggcaatgttt tccagctaga  1620
```

-continued

```
aacaaagact tgaaagacta tgaagcttgg cttggaatcc atgatgtcca tgagagaggc      1680
gaggagaaac gcaaacagat cttaaacatt tcccagctag tctatggacc tgaaggctca      1740
gatttggttt tactgaagct tgctcgccct gcaatcctgg ataactttgt cagtacaatt      1800
gatttaccta gttatggctg tacaatccct gaaaagacta cttgcagtat ttacggctgg      1860
ggctacactg gattgatcaa cgcagatggt ttattacgag tagctcatct gtatattatg      1920
gggaatgaga aatgcagtca gcaccatcaa ggcaaggtga ctttgaatga gtctgaatta      1980
tgtgctgggg ctgaaaagat tggatcagga ccttgtgagg gagattatgg tggcccactc      2040
atttgtgaac aacacaaaat gagaatggtt cttggtgtca ttgttcctgg tcgtggatgt      2100
gccatcccaa atcgtcctgg tatttttgtt cgagtagcat attatgcaaa atggatacac      2160
aaagtaattt tgacatacaa gttgtaa                                          2187
```

<210> SEQ ID NO 6
<211> LENGTH: 728
<212> TYPE: PRT
<213> ORGANISM: Rattus norvegicus

<400> SEQUENCE: 6

```
Met Met Trp Gly Thr Lys Leu Leu Pro Val Leu Leu Gln His Val
1               5                   10                  15

Leu Leu His Leu Leu Leu Pro Val Thr Ile Pro Tyr Ala Glu Gly
                20                  25                  30

Gln Lys Lys Arg Arg Asn Thr Leu His Glu Phe Lys Ser Ala Lys
            35                  40                  45

Thr Thr Leu Thr Lys Glu Asp Pro Leu Val Lys Ile Lys Thr Lys
    50                  55                      60

Val Asn Ser Ala Asp Glu Cys Ala Asn Arg Cys Ile Arg Asn Lys Gly
65                  70                      75                  80

Phe Pro Phe Thr Cys Lys Ala Phe Val Phe Asp Lys Ser Arg Lys Arg
                85                      90                  95

Cys Tyr Trp Tyr Pro Phe Asn Ser Met Ser Ser Gly Val Lys Lys Gly
                100                 105                 110

Phe Gly His Glu Phe Asp Leu Tyr Glu Asn Lys Asp Tyr Ile Arg Asn
            115                 120                 125

Cys Ile Ile Gly Lys Gly Gly Ser Tyr Lys Gly Thr Val Ser Ile Thr
        130                 135                 140

Lys Ser Gly Ile Lys Cys Gln Pro Trp Asn Ser Met Ile Pro His Glu
145                 150                 155                 160

His Ser Phe Leu Pro Ser Ser Tyr Arg Gly Lys Asp Leu Gln Glu Asn
                165                 170                 175

Tyr Cys Arg Asn Pro Arg Gly Glu Glu Gly Gly Pro Trp Cys Phe Thr
            180                 185                 190

Ser Asn Pro Glu Val Arg Tyr Glu Val Cys Asp Ile Pro Gln Cys Ser
        195                 200                 205

Glu Val Glu Cys Met Thr Cys Asn Gly Glu Ser Tyr Arg Gly Pro Met
    210                 215                 220

Asp His Thr Glu Ser Gly Lys Thr Cys Gln Arg Trp Asp Gln Gln Thr
225                 230                 235                 240

Pro His Arg His Lys Phe Leu Pro Glu Arg Tyr Pro Asp Lys Gly Phe
                245                 250                 255

Asp Asp Asn Tyr Cys Arg Asn Pro Asp Gly Lys Pro Arg Pro Trp Cys
            260                 265                 270
```

-continued

```
Tyr Thr Leu Asp Pro Asp Thr Pro Trp Glu Tyr Cys Ala Ile Lys Met
            275                 280                 285
Cys Ala His Ser Ala Val Asn Glu Thr Asp Val Pro Met Glu Thr Thr
        290                 295                 300
Glu Cys Ile Lys Gly Gln Gly Glu Gly Tyr Arg Gly Thr Thr Asn Thr
305                 310                 315                 320
Ile Trp Asn Gly Ile Pro Cys Gln Arg Trp Asp Ser Gln Tyr Pro His
                325                 330                 335
Lys His Asp Ile Thr Pro Glu Asn Phe Lys Cys Lys Asp Leu Arg Glu
            340                 345                 350
Asn Tyr Cys Arg Asn Pro Asp Gly Ala Glu Ser Pro Trp Cys Phe Thr
        355                 360                 365
Thr Asp Pro Asn Ile Arg Val Gly Tyr Cys Ser Gln Ile Pro Lys Cys
    370                 375                 380
Asp Val Ser Ser Gly Gln Asp Cys Tyr Arg Gly Asn Gly Lys Asn Tyr
385                 390                 395                 400
Met Gly Asn Leu Ser Lys Thr Arg Ser Gly Leu Thr Cys Ser Met Trp
                405                 410                 415
Asp Lys Asn Met Glu Asp Leu His Arg His Ile Phe Trp Glu Pro Asp
            420                 425                 430
Ala Ser Lys Leu Thr Lys Asn Tyr Cys Arg Asn Pro Asp Asp Asp Ala
        435                 440                 445
His Gly Pro Trp Cys Tyr Thr Gly Asn Pro Leu Val Pro Trp Asp Tyr
    450                 455                 460
Cys Pro Ile Ser Arg Cys Glu Gly Asp Thr Thr Pro Thr Ile Val Asn
465                 470                 475                 480
Leu Asp His Pro Val Ile Ser Cys Ala Lys Thr Lys Gln Leu Arg Val
                485                 490                 495
Val Asn Gly Ile Pro Thr Gln Thr Thr Val Gly Trp Met Val Ser Leu
            500                 505                 510
Lys Tyr Arg Asn Lys His Ile Cys Gly Gly Ser Leu Ile Lys Glu Ser
        515                 520                 525
Trp Val Leu Thr Ala Arg Gln Cys Phe Pro Ala Arg Asn Lys Asp Leu
    530                 535                 540
Lys Asp Tyr Glu Ala Trp Leu Gly Ile His Asp Val His Glu Arg Gly
545                 550                 555                 560
Glu Glu Lys Arg Lys Gln Ile Leu Asn Ile Ser Gln Leu Val Tyr Gly
                565                 570                 575
Pro Glu Gly Ser Asp Leu Val Leu Leu Lys Leu Ala Arg Pro Ala Ile
            580                 585                 590
Leu Asp Asn Phe Val Ser Thr Ile Asp Leu Pro Ser Tyr Gly Cys Thr
        595                 600                 605
Ile Pro Glu Lys Thr Thr Cys Ser Ile Tyr Gly Trp Gly Tyr Thr Gly
    610                 615                 620
Leu Ile Asn Ala Asp Gly Leu Leu Arg Val Ala His Leu Tyr Ile Met
625                 630                 635                 640
Gly Asn Glu Lys Cys Ser Gln His His Gln Gly Lys Val Thr Leu Asn
                645                 650                 655
Glu Ser Glu Leu Cys Ala Gly Ala Glu Lys Ile Gly Ser Gly Pro Cys
            660                 665                 670
Glu Gly Asp Tyr Gly Gly Pro Leu Ile Cys Glu Gln His Lys Met Arg
        675                 680                 685
Met Val Leu Gly Val Ile Val Pro Gly Arg Gly Cys Ala Ile Pro Asn
```

Arg Pro Gly Ile Phe Val Arg Val Ala Tyr Tyr Ala Lys Trp Ile His
705                 710                 715                 720

Lys Val Ile Leu Thr Tyr Lys Leu
            725

<210> SEQ ID NO 7
<211> LENGTH: 2187
<212> TYPE: DNA
<213> ORGANISM: Felis catus

<400> SEQUENCE: 7

| | | | | | |
|---|---|---|---|---|---|
| atgtgggtga | ccaaacttct | tccagtcctg | ctgctgcagc | acgtcctcct | ccacctcctt | 60 |
| ctgcttccca | tccctatgc | agaaggacag | aagaaaagaa | gaaacacact | tcatgaattc | 120 |
| aaaaagtcag | caaagactac | tctaattaaa | gaagacccat | tactgaagat | aaaaacaaaa | 180 |
| aaaatgaaca | ctgcagacca | atgtgccaat | agatgtatta | ggaataaagg | acttccattc | 240 |
| acttgcaagg | cctttgtttt | tgataaagca | aggaaacgat | gcctctggtt | ccctttcaat | 300 |
| agcatgacaa | gtggagtgaa | aaagagtttt | ggtcatgaat | tcgatctcta | tgaaaacaaa | 360 |
| gactacatta | gaaactgcat | cattggcaaa | ggaggtagcc | acaagggaac | agtatctatc | 420 |
| actaagagtg | gcatcaaatg | ccagccttgg | aattctatga | taccacatga | acacagcttt | 480 |
| ttgccttcga | gctatcgggg | taaagaccta | caggaaaact | actgtcgaaa | tcctcgaggg | 540 |
| gaagaagggg | gaccttggtg | tttcacaagc | aatccagagg | tacgctacga | agtctgtgac | 600 |
| attcctcagt | gttcagaagt | tgaatgcatg | acctgcaatg | ggaaagttta | tcgaggtccc | 660 |
| atggatcata | cagaatcagg | caagatttgt | cagcgctggg | atcgtcagac | accacaccgg | 720 |
| cacaaattct | tgccagaaag | atatcccgac | aagggctttg | atgataatta | ttgccgcaat | 780 |
| cctgatggca | agccgaggcc | atggtgctat | actcttgacc | ctgacacccc | ctgggagtac | 840 |
| tgtgcaatta | aaatgtgcgc | tcacagtact | atgaatgaca | cagatgtgcc | tatgaaaaca | 900 |
| actgaatgca | ttcagggtca | aggagaaggt | taccggggca | ccatcaactc | catctggaat | 960 |
| ggagttccat | gtcagcgttg | ggattcccag | tatcctcacc | agcatgacat | aactcctgaa | 1020 |
| aatttcaagt | gcaaggacct | acgagaaaat | ttttgccgaa | atccagatgg | agctgagtca | 1080 |
| ccctggtgtt | ttaccactga | tccaaacatc | cgagttggct | actgctccca | aattccaaaa | 1140 |
| tgtgatgtgt | cgagtggaca | agattgttat | cgtgggaatg | gcaaaaatta | tatgggcaat | 1200 |
| ttatccaaaa | cacgatctgg | actaacatgt | tcaatgtggg | agaagaacat | ggaagactta | 1260 |
| cacaggcata | tcttctggga | accagatgct | agtaagctga | ataagaatta | ctgccggaat | 1320 |
| cctgatgatg | atgcccatgg | cccctggtgt | tacacgggaa | atcctctcat | tccatgggat | 1380 |
| tattgtccta | tttctcgttg | tgaaggtgat | accacaccta | caatagtcaa | tttagaccat | 1440 |
| cccgtaatat | cttgtgccaa | aacaaaacaa | ctgcgagttg | taaatggaat | cccaacgcgg | 1500 |
| acaaatgtag | gatggatggt | tagtttgaaa | tacagaaata | acatatctg | tggaggatca | 1560 |
| ttgataaagg | aaagttggat | tcttaccgca | agacaatgtt | tcccttctcg | aaacaaagac | 1620 |
| ttgaaagatt | acgaagcttg | gcttgggatt | catgatgtcc | acggaagagg | agatgagaaa | 1680 |
| cgcaaacagg | ttctaaatgt | gtcccagctg | gtatatgggc | ctgaagggtc | agatctggta | 1740 |
| ttactgaagc | ttgctaggcc | tgctgtcctg | gatgattttg | ttagtacaat | tgatttacct | 1800 |
| aattatggat | gcaccattcc | tgaaaaaacc | acttgcagtg | tttatggctg | gggttatact | 1860 |
| ggatcaatca | actctgatgg | tctattacga | gtagcacatc | tctatattat | ggggaatgag | 1920 |

```
aaatgcagcc aataccatca agggaaggtg actctgaatg agtctgaaat atgtgcaggt    1980
gccgaaaata ttgtgtcagg accatgtgag ggagattatg gtggcccact tgtttgtgaa    2040
caacataaaa tgagaatggt ccttggtgtc attgttcctg gtcgtggatg tgccattcca    2100
aatcgtcctg gcattttgt ccgagtagca tattatgcaa aatggataca caaaattata    2160
ttaacatata agataccaca gtcatag                                        2187
```

```
<210> SEQ ID NO 8
<211> LENGTH: 728
<212> TYPE: PRT
<213> ORGANISM: Felis catus

<400> SEQUENCE: 8

Met Trp Val Thr Lys Leu Leu Pro Val Leu Leu Gln His Val Leu
1               5                   10                  15

Leu His Leu Leu Leu Pro Ile Pro Tyr Ala Glu Gly Gln Lys Lys
                20                  25                  30

Arg Arg Asn Thr Leu His Glu Phe Lys Lys Ser Ala Lys Thr Thr Leu
                35                  40                  45

Ile Lys Glu Asp Pro Leu Leu Lys Ile Lys Thr Lys Lys Met Asn Thr
50                  55                  60

Ala Asp Gln Cys Ala Asn Arg Cys Ile Arg Asn Lys Gly Leu Pro Phe
65                  70                  75                  80

Thr Cys Lys Ala Phe Val Phe Asp Lys Ala Arg Lys Arg Cys Leu Trp
                85                  90                  95

Phe Pro Phe Asn Ser Met Thr Ser Gly Val Lys Lys Glu Phe Gly His
                100                 105                 110

Glu Phe Asp Leu Tyr Glu Asn Lys Asp Tyr Ile Arg Asn Cys Ile Ile
                115                 120                 125

Gly Lys Gly Gly Ser Tyr Lys Gly Thr Val Ser Ile Thr Lys Ser Gly
                130                 135                 140

Ile Lys Cys Gln Pro Trp Asn Ser Met Ile Pro His Glu His Ser Phe
145                 150                 155                 160

Leu Pro Ser Ser Tyr Arg Gly Lys Asp Leu Gln Glu Asn Tyr Cys Arg
                165                 170                 175

Asn Pro Arg Gly Glu Glu Gly Gly Pro Trp Cys Phe Thr Ser Asn Pro
                180                 185                 190

Glu Val Arg Tyr Glu Val Cys Asp Ile Pro Gln Cys Ser Glu Val Glu
                195                 200                 205

Cys Met Thr Cys Asn Gly Glu Ser Tyr Arg Gly Pro Met Asp His Thr
                210                 215                 220

Glu Ser Gly Lys Ile Cys Gln Arg Trp Asp Arg Gln Thr Pro His Arg
225                 230                 235                 240

His Lys Phe Leu Pro Glu Arg Tyr Pro Asp Lys Gly Phe Asp Asp Asn
                245                 250                 255

Tyr Cys Arg Asn Pro Asp Gly Lys Pro Arg Pro Trp Cys Tyr Thr Leu
                260                 265                 270

Asp Pro Asp Thr Pro Trp Glu Tyr Cys Ala Ile Lys Met Cys Ala His
                275                 280                 285

Ser Thr Met Asn Asp Thr Asp Val Pro Met Glu Thr Thr Glu Cys Ile
                290                 295                 300

Gln Gly Gln Gly Glu Gly Tyr Arg Gly Thr Ile Asn Ser Ile Trp Asn
305                 310                 315                 320
```

```
Gly Val Pro Cys Gln Arg Trp Asp Ser Gln Tyr Pro His Gln His Asp
            325                 330                 335

Ile Thr Pro Glu Asn Phe Lys Cys Lys Asp Leu Arg Glu Asn Phe Cys
            340                 345                 350

Arg Asn Pro Asp Gly Ala Glu Ser Pro Trp Cys Phe Thr Thr Asp Pro
            355                 360                 365

Asn Ile Arg Val Gly Tyr Cys Ser Gln Ile Pro Lys Cys Asp Val Ser
370                 375                 380

Ser Gly Gln Asp Cys Tyr Arg Gly Asn Gly Lys Asn Tyr Met Gly Asn
385                 390                 395                 400

Leu Ser Lys Thr Arg Ser Gly Leu Thr Cys Ser Met Trp Glu Lys Asn
            405                 410                 415

Met Glu Asp Leu His Arg His Ile Phe Trp Glu Pro Asp Ala Ser Lys
            420                 425                 430

Leu Asn Lys Asn Tyr Cys Arg Asn Pro Asp Asp Asp Ala His Gly Pro
            435                 440                 445

Trp Cys Tyr Thr Gly Asn Pro Leu Ile Pro Trp Asp Tyr Cys Pro Ile
450                 455                 460

Ser Arg Cys Glu Gly Asp Thr Thr Pro Thr Ile Val Asn Leu Asp His
465                 470                 475                 480

Pro Val Ile Ser Cys Ala Lys Thr Lys Gln Leu Arg Val Val Asn Gly
            485                 490                 495

Ile Pro Thr Arg Thr Asn Val Gly Trp Met Val Ser Leu Lys Tyr Arg
            500                 505                 510

Asn Lys His Ile Cys Gly Gly Ser Leu Ile Lys Glu Ser Trp Ile Leu
            515                 520                 525

Thr Ala Arg Gln Cys Phe Pro Ser Arg Asn Lys Asp Leu Lys Asp Tyr
            530                 535                 540

Glu Ala Trp Leu Gly Ile His Asp Val His Gly Arg Gly Asp Glu Lys
545                 550                 555                 560

Arg Lys Gln Val Leu Asn Val Ser Gln Leu Val Tyr Gly Pro Glu Gly
            565                 570                 575

Ser Asp Leu Val Leu Leu Lys Leu Ala Arg Pro Ala Val Leu Asp Asp
            580                 585                 590

Phe Val Ser Thr Ile Asp Leu Pro Asn Tyr Gly Cys Thr Ile Pro Glu
            595                 600                 605

Lys Thr Thr Cys Ser Val Tyr Gly Trp Gly Tyr Thr Gly Ser Ile Asn
            610                 615                 620

Ser Asp Gly Leu Leu Arg Val Ala His Leu Tyr Ile Met Gly Asn Glu
625                 630                 635                 640

Lys Cys Ser Gln Tyr His Gln Gly Lys Val Thr Leu Asn Glu Ser Glu
            645                 650                 655

Ile Cys Ala Gly Ala Glu Asn Ile Val Ser Gly Pro Cys Glu Gly Asp
            660                 665                 670

Tyr Gly Gly Pro Leu Val Cys Glu Gln His Lys Met Arg Met Val Leu
            675                 680                 685

Gly Val Ile Val Pro Gly Arg Gly Cys Ala Ile Pro Asn Arg Pro Gly
            690                 695                 700

Ile Phe Val Arg Val Ala Tyr Tyr Ala Lys Trp Ile His Lys Ile Ile
705                 710                 715                 720

Leu Thr Tyr Lys Ile Pro Gln Ser
            725
```

<210> SEQ ID NO 9
<211> LENGTH: 2193
<212> TYPE: DNA
<213> ORGANISM: Canis lupus familiaris

<400> SEQUENCE: 9

| | | | | | |
|---|---|---|---|---|---|
| atgtgggtga | ccaagctcct | gcccctgctg | gtgctgcagc | agctcctcct | gcacctcctc | 60 |
| ctgctgcccg | tcgccgtccc | ccgtgcagaa | ggacagaaga | aagaagaaa | cacacttcat | 120 |
| gaattcaaaa | agtcagcaaa | gactactcta | attaaagaag | acccattact | gaagataaaa | 180 |
| acaaaaaaaa | tgaacactgc | agaccaatgt | gccaatagat | gtattaggaa | taaaggactt | 240 |
| ccattcactt | gcaaggcctt | tgtttttgat | aaagcaagga | aacgatgcct | ctggttccct | 300 |
| ttcaatagca | tgacaagtgg | agtgaaaaaa | gagtttggtc | atgaatttga | tctctatgaa | 360 |
| aacaaagact | acattaggaa | ctgcatcatt | ggtaaaggag | gtagctacaa | ggggacagtg | 420 |
| tctatcacta | gagtggcat | caaatgccag | ccctggaatt | ccatgatacc | acatgaacac | 480 |
| agcttttgc | cttcgagcta | tcggggtaaa | gacctacagg | aaaactactg | tcgaaatcct | 540 |
| cgaggggaag | aaggggggacc | ttggtgtttc | acaagcaatc | cagaggtacg | ctacgaagtc | 600 |
| tgtgacattc | ctcagtgttc | agaagttgaa | tgcatgacct | gcaatgggga | aagttatcga | 660 |
| ggtcccatgg | atcacacaga | atcgggcaag | atttgtcagc | gctgggatca | tcagacaccg | 720 |
| caccggcaca | aattcttgcc | ggaaagatat | cccgacaagg | gctttgatga | taattattgc | 780 |
| cgcaaccctg | atggcaagcc | gaggccatgg | tgctatactc | ttgaccctga | cacccctgg | 840 |
| gagtactgtg | caattaaaat | gtgtgctcac | agtactatga | atgatacaga | tgtccctatg | 900 |
| gaaacaactg | aatgcattca | aggtcaagga | aaggttacc | ggggcaccat | caataccatt | 960 |
| tggaatggag | ttccgtgtca | gcgttgggat | tcccagtatc | ctcaccagca | tgacataact | 1020 |
| cctgaaaatt | tcaagtgcaa | ggacctaaga | gaaaattatt | gccgaaatcc | agatggggct | 1080 |
| gagtcaccct | ggtgttttac | cactgatcca | aacatccgag | ttggctactg | ctcccaaatt | 1140 |
| ccaaaatgtg | atgtgtcaag | tggacaagat | tgttatcggg | ggaatggcaa | aaattatatg | 1200 |
| ggcaatttat | ccaaaacacg | atctggacta | acatgttcaa | tgtgggagaa | gaacatggaa | 1260 |
| gacttacata | ggcatatctt | ctgggaacca | gatgctagta | agctgaataa | gaattactgc | 1320 |
| cggaatcctg | atgacgatgc | ccatggtccc | tggtgttaca | cgggaaatcc | tctcattcca | 1380 |
| tgggattatt | gtcctatttt | tcgttgtgaa | ggtgatacca | cacctacaat | agtcaattta | 1440 |
| gaccatcctg | taatatcttg | tgccaaaaca | aaacaattac | gagttgtaaa | tggaattcca | 1500 |
| acacggacta | atgtaggatg | gatggttagt | ttgaaataca | gaaataaaca | tatctgtgga | 1560 |
| ggatcattga | taaaggaaag | ttggattctt | actgcaagac | aatgtttccc | ctctcgaaac | 1620 |
| agagacttga | agattatga | agcttggctt | gggattcatg | acgtccacgg | aaaaggagat | 1680 |
| gagaaacgca | aacaggttct | gaatgttttcc | cagctggtat | atgggcctga | aggatcagat | 1740 |
| ctggtattac | tgaagcttgc | taggcccgct | atcctggatg | attttgttag | tacaatcgat | 1800 |
| ttacctaatt | atggatgcac | cattcctgaa | aaaccactt | gcagtgttta | tggctggggt | 1860 |
| tatactggat | cgatcaactt | tgatggtcta | ttacgagtag | cacatctcta | tattatgggg | 1920 |
| aatgagaaat | gcagccaata | ccatcaaggg | aaggtgacac | tgaatgagtc | tgaaatatgt | 1980 |
| gctggagctg | aaaatattgt | atcaggacca | tgtgagggag | attatggtgg | cccacttgtt | 2040 |
| tgcgaacaac | ataaaatgag | gatggttctt | ggcgtcattg | ttcctggtcg | tggatgtgcc | 2100 |
| attccaaatc | gtcctggcat | ttttgtccga | gtagcatatt | atgcaaaatg | gatacacaaa | 2160 | attatattaa cgtataagat acaacagtca tag 2193

<210> SEQ ID NO 10
<211> LENGTH: 730
<212> TYPE: PRT
<213> ORGANISM: Canis lupus familiaris

<400> SEQUENCE: 10

| | | | | | | | | | | | | | | |
|---|---|---|---|---|---|---|---|---|---|---|---|---|---|---|
| Met | Trp | Val | Thr | Lys | Leu | Leu | Pro | Leu | Leu | Val | Leu | Gln | Gln | Leu | Leu |
| 1 | | | | 5 | | | | | 10 | | | | | 15 | |
| Leu | His | Leu | Leu | Leu | Leu | Pro | Val | Ala | Val | Pro | Arg | Ala | Glu | Gly | Gln |
| | | | 20 | | | | | 25 | | | | | 30 | | |
| Lys | Lys | Arg | Arg | Asn | Thr | Leu | His | Glu | Phe | Lys | Lys | Ser | Ala | Lys | Thr |
| | | | 35 | | | | | 40 | | | | | 45 | | |
| Thr | Leu | Ile | Lys | Glu | Asp | Pro | Leu | Leu | Lys | Ile | Lys | Thr | Lys | Lys | Met |
| | 50 | | | | | 55 | | | | | 60 | | | | |
| Asn | Thr | Ala | Asp | Gln | Cys | Ala | Asn | Arg | Cys | Ile | Arg | Asn | Lys | Gly | Leu |
| 65 | | | | | 70 | | | | | 75 | | | | | 80 |
| Pro | Phe | Thr | Cys | Lys | Ala | Phe | Val | Phe | Asp | Lys | Ala | Arg | Lys | Arg | Cys |
| | | | | 85 | | | | | 90 | | | | | 95 | |
| Leu | Trp | Phe | Pro | Phe | Asn | Ser | Met | Thr | Ser | Gly | Val | Lys | Lys | Glu | Phe |
| | | | 100 | | | | | 105 | | | | | 110 | | |
| Gly | His | Glu | Phe | Asp | Leu | Tyr | Glu | Asn | Lys | Asp | Tyr | Ile | Arg | Asn | Cys |
| | | | 115 | | | | | 120 | | | | | 125 | | |
| Ile | Ile | Gly | Lys | Gly | Gly | Ser | Tyr | Lys | Gly | Thr | Val | Ser | Ile | Thr | Lys |
| | 130 | | | | | 135 | | | | | 140 | | | | |
| Ser | Gly | Ile | Lys | Cys | Gln | Pro | Trp | Asn | Ser | Met | Ile | Pro | His | Glu | His |
| 145 | | | | | 150 | | | | | 155 | | | | | 160 |
| Ser | Phe | Leu | Pro | Ser | Ser | Tyr | Arg | Gly | Lys | Asp | Leu | Gln | Glu | Asn | Tyr |
| | | | | 165 | | | | | 170 | | | | | 175 | |
| Cys | Arg | Asn | Pro | Arg | Gly | Glu | Glu | Gly | Gly | Pro | Trp | Cys | Phe | Thr | Ser |
| | | | 180 | | | | | 185 | | | | | 190 | | |
| Asn | Pro | Glu | Val | Arg | Tyr | Glu | Val | Cys | Asp | Ile | Pro | Gln | Cys | Ser | Glu |
| | | | 195 | | | | | 200 | | | | | 205 | | |
| Val | Glu | Cys | Met | Thr | Cys | Asn | Gly | Glu | Ser | Tyr | Arg | Gly | Pro | Met | Asp |
| | 210 | | | | | 215 | | | | | 220 | | | | |
| His | Thr | Glu | Ser | Gly | Lys | Ile | Cys | Gln | Arg | Trp | Asp | His | Gln | Thr | Pro |
| 225 | | | | | 230 | | | | | 235 | | | | | 240 |
| His | Arg | His | Lys | Phe | Leu | Pro | Glu | Arg | Tyr | Pro | Asp | Lys | Gly | Phe | Asp |
| | | | | 245 | | | | | 250 | | | | | 255 | |
| Asp | Asn | Tyr | Cys | Arg | Asn | Pro | Asp | Gly | Lys | Pro | Arg | Pro | Trp | Cys | Tyr |
| | | | 260 | | | | | 265 | | | | | 270 | | |
| Thr | Leu | Asp | Pro | Asp | Thr | Pro | Trp | Glu | Tyr | Cys | Ala | Ile | Lys | Met | Cys |
| | | | 275 | | | | | 280 | | | | | 285 | | |
| Ala | His | Ser | Thr | Met | Asn | Asp | Thr | Asp | Val | Pro | Met | Glu | Thr | Thr | Glu |
| | 290 | | | | | 295 | | | | | 300 | | | | |
| Cys | Ile | Gln | Gly | Gln | Gly | Glu | Gly | Tyr | Arg | Gly | Thr | Ile | Asn | Thr | Ile |
| 305 | | | | | 310 | | | | | 315 | | | | | 320 |
| Trp | Asn | Gly | Val | Pro | Cys | Gln | Arg | Trp | Asp | Ser | Gln | Tyr | Pro | His | Gln |
| | | | | 325 | | | | | 330 | | | | | 335 | |
| His | Asp | Ile | Thr | Pro | Glu | Asn | Phe | Lys | Cys | Lys | Asp | Leu | Arg | Glu | Asn |
| | | | 340 | | | | | 345 | | | | | 350 | | |
| Tyr | Cys | Arg | Asn | Pro | Asp | Gly | Ala | Glu | Ser | Pro | Trp | Cys | Phe | Thr | Thr |
| | | | 355 | | | | | 360 | | | | | 365 | | |

```
Asp Pro Asn Ile Arg Val Gly Tyr Cys Ser Gln Ile Pro Lys Cys Asp
    370                 375                 380
Val Ser Ser Gly Gln Asp Cys Tyr Arg Gly Asn Gly Lys Asn Tyr Met
385                 390                 395                 400
Gly Asn Leu Ser Lys Thr Arg Ser Gly Leu Thr Cys Ser Met Trp Glu
                405                 410                 415
Lys Asn Met Glu Asp Leu His Arg His Ile Phe Trp Glu Pro Asp Ala
            420                 425                 430
Ser Lys Leu Asn Lys Asn Tyr Cys Arg Asn Pro Asp Asp Ala His
        435                 440                 445
Gly Pro Trp Cys Tyr Thr Gly Asn Pro Leu Ile Pro Trp Asp Tyr Cys
450                 455                 460
Pro Ile Phe Arg Cys Glu Gly Asp Thr Thr Pro Thr Ile Val Asn Leu
465                 470                 475                 480
Asp His Pro Val Ile Ser Cys Ala Lys Thr Lys Gln Leu Arg Val Val
                485                 490                 495
Asn Gly Ile Pro Thr Arg Thr Asn Val Gly Trp Met Val Ser Leu Lys
            500                 505                 510
Tyr Arg Asn Lys His Ile Cys Gly Gly Ser Leu Ile Lys Glu Ser Trp
        515                 520                 525
Ile Leu Thr Ala Arg Gln Cys Phe Pro Ser Arg Asn Arg Asp Leu Lys
530                 535                 540
Asp Tyr Glu Ala Trp Leu Gly Ile His Asp Val His Gly Lys Gly Asp
545                 550                 555                 560
Glu Lys Arg Lys Gln Val Leu Asn Val Ser Gln Leu Val Tyr Gly Pro
                565                 570                 575
Glu Gly Ser Asp Leu Val Leu Leu Lys Leu Ala Arg Pro Ala Ile Leu
            580                 585                 590
Asp Asp Phe Val Ser Thr Ile Asp Leu Pro Asn Tyr Gly Cys Thr Ile
        595                 600                 605
Pro Glu Lys Thr Thr Cys Ser Val Tyr Gly Trp Gly Tyr Thr Gly Ser
610                 615                 620
Ile Asn Phe Asp Gly Leu Leu Arg Val Ala His Leu Tyr Ile Met Gly
625                 630                 635                 640
Asn Glu Lys Cys Ser Gln Tyr His Gln Gly Lys Val Thr Leu Asn Glu
                645                 650                 655
Ser Glu Ile Cys Ala Gly Ala Glu Asn Ile Val Ser Gly Pro Cys Glu
            660                 665                 670
Gly Asp Tyr Gly Gly Pro Leu Val Cys Glu Gln His Lys Met Arg Met
        675                 680                 685
Val Leu Gly Val Ile Val Pro Gly Arg Gly Cys Ala Ile Pro Asn Arg
690                 695                 700
Pro Gly Ile Phe Val Arg Val Ala Tyr Tyr Ala Lys Trp Ile His Lys
705                 710                 715                 720
Ile Ile Leu Thr Tyr Lys Ile Gln Gln Ser
                725                 730

<210> SEQ ID NO 11
<211> LENGTH: 2193
<212> TYPE: DNA
<213> ORGANISM: Bos taurus

<400> SEQUENCE: 11
atgtgggtga ccagacttct gccagtcctg ctgctgcagc acgtcctcct ccacctcctc    60
```

| | |
|---|---|
| ctgcttccca tcgccatccc ctatgcagaa ggacagaaga aaagaagaaa cacacttcat | 120 |
| gaattcaaaa ggtcagcaaa gactactcta attaaagagg acccattact gaagataaaa | 180 |
| acaaaaaaaa tgaacactgc agaccaatgt gccaatagat gtattaggaa taaaggactt | 240 |
| ccattcactt gcaaggcctt tgtttttgat aaagcaagaa aacgatgcct ctggttccct | 300 |
| ttcaatagca tgtcaagtgg agtaaaaaaa gagtttggcc atgaatttga cctctatgaa | 360 |
| aacaaagact acattagaaa ctgtatcatt ggtaaaggcg gtagctacaa ggggacggta | 420 |
| tctatcacta aaagtggcat caaatgtcag ccctggaatt ccatgatacc acacgaacac | 480 |
| agcttttttgc cttcgagcta tcggggtaaa gacctacagg aaaactactg tcgaaatcct | 540 |
| cgaggggaag aaggggggacc ttggtgtttc acaagcaatc cagaggtacg ctacgaagtc | 600 |
| tgtgacattc ctcagtgttc agaagttgaa tgcatgacct gcaatgggga agttaccga | 660 |
| ggtcccatgg atcacacaga aacaggcaag atttgtcagc gctgggatca tcagacacca | 720 |
| caccggcaca aattcttgcc agaaagatat cctgacaagg gctttgatga taattattgc | 780 |
| cgcaatcctg atggcaagcc gaggccatgg tgctatactc ttgaccctga cacccccttgg | 840 |
| gagtactgtg caattaaaat gtgcgcccac agtactatga atgacacaga tctccctatg | 900 |
| caaacgactg aatgcattca aggtcaagga aaggttacc ggggcaccat cataccatt | 960 |
| tggaatggaa ttccctgtca gcgttgggat tcccagtatc ctcaccagca tgacataact | 1020 |
| cctgaaaatt tcaagtgcaa ggacctaaga gaaaattatt gccgaaatcc agatggggct | 1080 |
| gagtcaccgt ggtgttttac cactgatcca aacatccgag ttggctactg ctcccaaatt | 1140 |
| ccaaaatgtg acgtgtcaag tggacaagat tgttatcgtg gaatggcaa aaactatatg | 1200 |
| ggcagtttat ccaaaacacg atctggacta acatgttcga tgtgggataa gaacatggaa | 1260 |
| gatttacacc ggcatatctt ctgggaacca gatgctacta agctgaataa gaattactgt | 1320 |
| cggaatcctg atgacgatgc ccacggtccc tggtgttaca cagggaatcc tctcattcct | 1380 |
| tgggattatt gccctatttc tcgttgtgag ggcgatacca cacctacaat agtcaattta | 1440 |
| gaccatccag taatatcttg cgccaaaaca aaacagttgc gagttgtaaa tggaattcca | 1500 |
| acacgaacaa atgtaggatg gatggttagt ttgaaataca gaaataaaca tatctgcgga | 1560 |
| ggatcattga taaaggaaag ttggattctt actgcaagac agtgtttccc ttctcgaaac | 1620 |
| aaggacttga agattatga agcttggctt ggaattcatg atgtccatgg gagaggagat | 1680 |
| gagaaacgca acaggttct aaatgttacc caactggtat atgggcctga aggatcagat | 1740 |
| ctggtattac tgaagcttgc taggcctgct attttggatg attttgttag tacaattgat | 1800 |
| ttacctaatt atgggtgcac aattcctgag aaaaccactt gcagtgttta tggctggggc | 1860 |
| tacactggat tgatcaactc agatggtcta ctacgagtag cacatctcta tattatgggg | 1920 |
| aatgagaaat gcagccaata tcatcaaggg aaggtgactc tgaatgagtc tgaaatatgt | 1980 |
| gctgggctg aaaatattgt atcaggacca tgtgagggag attatggtgg cccacttgtt | 2040 |
| tgtgaacaac ataaaatgag aatggttctt ggtgtcattg ttcctggtcg tggctgtgcc | 2100 |
| attccaaacc gtcctggtat ttttgtccga gtggcatatt atgcaaaatg gatacacaaa | 2160 |
| atcatattaa cgtataaggc accacagttg tag | 2193 |

<210> SEQ ID NO 12
<211> LENGTH: 730
<212> TYPE: PRT
<213> ORGANISM: Bos taurus

<400> SEQUENCE: 12

```
Met Trp Val Thr Arg Leu Leu Pro Val Leu Leu Gln His Val Leu
1               5                   10                  15

Leu His Leu Leu Leu Leu Pro Ile Ala Ile Pro Tyr Ala Glu Gly Gln
                20                  25                  30

Lys Lys Arg Arg Asn Thr Leu His Glu Phe Lys Arg Ser Ala Lys Thr
            35                  40                  45

Thr Leu Ile Lys Glu Asp Pro Leu Leu Lys Ile Lys Thr Lys Lys Met
        50                  55                  60

Asn Thr Ala Asp Gln Cys Ala Asn Arg Cys Ile Arg Asn Lys Gly Leu
65                  70                  75                  80

Pro Phe Thr Cys Lys Ala Phe Val Phe Asp Lys Ala Arg Lys Arg Cys
                85                  90                  95

Leu Trp Phe Pro Phe Asn Ser Met Ser Ser Gly Val Lys Lys Glu Phe
                100                 105                 110

Gly His Glu Phe Asp Leu Tyr Glu Asn Lys Asp Tyr Ile Arg Asn Cys
            115                 120                 125

Ile Ile Gly Lys Gly Gly Ser Tyr Lys Gly Thr Val Ser Ile Thr Lys
        130                 135                 140

Ser Gly Ile Lys Cys Gln Pro Trp Asn Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
                180                 185                 190

Asn Pro Glu Val Arg Tyr Glu Val Cys Asp Ile Pro Gln Cys Ser Glu
            195                 200                 205

Val Glu Cys Met Thr Cys Asn Gly Glu Ser Tyr Arg Gly Pro Met Asp
        210                 215                 220

His Thr Glu Thr Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Lys Pro Arg Pro Trp Cys Tyr
            260                 265                 270

Thr Leu Asp Pro Asp Thr Pro Trp Glu Tyr Cys Ala Ile Lys Met Cys
        275                 280                 285

Ala His Ser Thr Met Asn Asp Thr Asp Leu Pro Met Gln Thr Thr Glu
        290                 295                 300

Cys Ile Gln Gly Gln Gly Glu Gly Tyr Arg Gly Thr Ile Asn Thr Ile
305                 310                 315                 320

Trp Asn Gly Ile Pro Cys Gln Arg Trp Asp Ser Gln Tyr Pro His Gln
                325                 330                 335

His Asp Ile Thr Pro Glu Asn Phe Lys Cys Lys Asp Leu Arg Glu Asn
            340                 345                 350

Tyr Cys Arg Asn Pro Asp Gly Ala Glu Ser Pro Trp Cys Phe Thr Thr
            355                 360                 365

Asp Pro Asn Ile Arg Val Gly Tyr Cys Ser Gln Ile Pro Lys Cys Asp
370                 375                 380

Val Ser Ser Gly Gln Asp Cys Tyr Arg Gly Asn Gly Lys Asn Tyr Met
385                 390                 395                 400

Gly Ser Leu Ser Lys Thr Arg Ser Gly Leu Thr Cys Ser Met Trp Asp
                405                 410                 415
```

```
Lys Asn Met Glu Asp Leu His Arg His Ile Phe Trp Glu Pro Asp Ala
            420                 425                 430

Thr Lys Leu Asn Lys Asn Tyr Cys Arg Asn Pro Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Val Gly Trp Met Val Ser Leu Lys
                500                 505                 510

Tyr Arg Asn Lys His Ile Cys Gly Gly Ser Leu Ile Lys Glu Ser Trp
            515                 520                 525

Ile Leu Thr Ala Arg Gln Cys Phe Pro Ser Arg Asn Lys Asp Leu Lys
        530                 535                 540

Asp Tyr Glu Ala Trp Leu Gly Ile His Asp Val His Gly Arg Gly Asp
545                 550                 555                 560

Glu Lys Arg Lys Gln Val Leu Asn Val Thr Gln Leu Val Tyr Gly Pro
                565                 570                 575

Glu Gly Ser Asp Leu Val Leu Leu Lys Leu Ala Arg Pro Ala Ile Leu
            580                 585                 590

Asp Asp Phe Val Ser Thr Ile Asp Leu Pro Asn Tyr Gly Cys Thr Ile
        595                 600                 605

Pro Glu Lys Thr Thr Cys Ser Val Tyr Gly Trp Gly Tyr Thr Gly Leu
610                 615                 620

Ile Asn Ser Asp Gly Leu Leu Arg Val Ala His Leu Tyr Ile Met Gly
625                 630                 635                 640

Asn Glu Lys Cys Ser Gln Tyr His Gln Gly Lys Val Thr Leu Asn Glu
                645                 650                 655

Ser Glu Ile Cys Ala Gly Ala Glu Asn Ile Val Ser Gly Pro Cys Glu
            660                 665                 670

Gly Asp Tyr Gly Gly Pro Leu Val Cys Glu Gln His Lys Met Arg Met
        675                 680                 685

Val Leu Gly Val Ile Val Pro Gly Arg Gly Cys Ala Ile Pro Asn Arg
690                 695                 700

Pro Gly Ile Phe Val Arg Val Ala Tyr Tyr Ala Lys Trp Ile His Lys
705                 710                 715                 720

Ile Ile Leu Thr Tyr Lys Ala Pro Gln Leu
                725                 730

<210> SEQ ID NO 13
<211> LENGTH: 24
<212> TYPE: DNA
<213> ORGANISM: Artificial
<220> FEATURE:
<223> OTHER INFORMATION: primer

<400> SEQUENCE: 13
gacatgttca gctttgtgga cctc                                    24

<210> SEQ ID NO 14
<211> LENGTH: 22
<212> TYPE: DNA
<213> ORGANISM: Artificial
<220> FEATURE:
<223> OTHER INFORMATION: primer
```

<400> SEQUENCE: 14
gggaccctta ggccattgtg ta                    22

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
tgcgcctgca gagattcaag                    20

<210> SEQ ID NO 16
<211> LENGTH: 24
<212> TYPE: DNA
<213> ORGANISM: Artificial
<220> FEATURE:
<223> OTHER INFORMATION: primer

<400> SEQUENCE: 16
acgtaacgcc aggaattgtt gcta                    24

<210> SEQ ID NO 17
<211> LENGTH: 24
<212> TYPE: DNA
<213> ORGANISM: Artificial
<220> FEATURE:
<223> OTHER INFORMATION: primer

<400> SEQUENCE: 17
cgagaccacc ttataccagc gtta                    24

<210> SEQ ID NO 18
<211> LENGTH: 20
<212> TYPE: DNA
<213> ORGANISM: Artificial
<220> FEATURE:
<223> OTHER INFORMATION: primer

<400> SEQUENCE: 18
tgatgtgcaa atttcgttcc                    20

<210> SEQ ID NO 19
<211> LENGTH: 22
<212> TYPE: DNA
<213> ORGANISM: Artificial
<220> FEATURE:
<223> OTHER INFORMATION: primer

<400> SEQUENCE: 19
gacacgctta gcatcaccca ga                    22

<210> SEQ ID NO 20
<211> LENGTH: 22
<212> TYPE: DNA
<213> ORGANISM: Artificial
<220> FEATURE:
<223> OTHER INFORMATION: primer

<400> SEQUENCE: 20
ctgtgaccca gtccatccag ag                    22

<210> SEQ ID NO 21

```
<211> LENGTH: 22
<212> TYPE: DNA
<213> ORGANISM: Artificial
<220> FEATURE:
<223> OTHER INFORMATION: primer

<400> SEQUENCE: 21
ggcacagtca aggctgagaa tg                                              22

<210> SEQ ID NO 22
<211> LENGTH: 18
<212> TYPE: DNA
<213> ORGANISM: Artificial
<220> FEATURE:
<223> OTHER INFORMATION: primer

<400> SEQUENCE: 22
atggtgaaga cgccagta                                                   18
```

PHARMACEUTICAL COMPOSITION FOR TREATING AND/OR PREVENTING ESOPHAGEAL STENOSIS

CROSS-REFERENCE TO RELATED APPLICATIONS

This application is a National Stage application of PCT/JP2015/072385, filed Aug. 6, 2015, which claims priority from Japanese application JP 2014-164429, filed Aug. 12, 2014.

TECHNICAL FIELD

The present invention relates to a pharmaceutical composition for treating and/or preventing esophageal stenosis, comprising a hepatocyte growth factor (HGF) protein as an active ingredient.

In esophagus, esophageal stenosis often occurs after endoscopic submucosal dissection for cases of early esophageal cancer (i.e., superficial esophageal cancer). Endoscopic balloon dilatation is adopted for such esophageal stenosis occurring after submucosal dissection. However, dilation needs to be performed several times in order to improve symptoms of stenosis such as dysphagia. In addition, even when it is possible to dilate the esophagus, stenosis tends to recur easily.

Thus far, there have been no known effective means other than endoscopic balloon dilatation for esophageal stenosis occurring after submucosal dissection.

Meanwhile, HGF is a growth factor capable of strongly promoting lung regeneration. HGF was isolated by Tsubouchi and Gohda et al. from the plasma of fulminant hepatitis patients in 1986 (Non-Patent Literature 1), and human cDNA thereof was cloned in 1989 (Non-Patent Literature 2). HGF exerts a variety of actions, such as causing cell proliferation of not only stem cells but also various epithelial cells, endothelial cells, and some mesenchymal cells. Moreover, HGF is an important repair factor for gastrointestinal tract mucosal injury, and the ability thereof to promote restoration of mucosal injuries was confirmed in experimental colitis models using recombinant human HGF (Non-Patent Literature 3-5).

However, it has thus far remained unknown that HGF is effective for gastrointestinal stenosis.

CITATION LIST

Non-Patent Literature

Non-Patent Literature 1: Gohda E, Tsubouchi H, et al., J Clin Invest. 1988; 81: 414-419
Non-Patent Literature 2: Miyazawa K, Tsubouchi H, et al., Biochem Biophys Res Commun. 1989; 163: 967-973
Non-Patent Literature 3: Tahara Y, Ido A, et al., J Pharmacol Exp Ther. 2003; 307: 146-151
Non-Patent Literature 4: Numata M, Ido A, et al., Inflamm Bowel Dis. 2005; 11: 551-558
Non-Patent Literature 5: Setoyama H, et al., Life Sci. 2011; 89: 269-275

SUMMARY OF INVENTION

Technical Problem

An object of the present invention is to provide a pharmaceutical composition for treating and/or preventing esophageal stenosis.

Solution to Problem

As a result of intensive studies in order to find a medicine for treating and/or preventing esophageal stenosis, the present inventors found that the HGF protein can inhibit or improve esophageal stenosis. This has led to the completion of the present invention. Accordingly, the present invention encompasses the following features.

1. A pharmaceutical composition for treating and/or preventing esophageal stenosis, comprising a hepatocyte growth factor (HGF) protein as an active ingredient.
2. The pharmaceutical composition according to 1 above, wherein the esophageal stenosis is esophageal stenosis occurring after endoscopic submucosal dissection.
3. The pharmaceutical composition according to 1 or 2 above, wherein the HGF protein is a human HGF protein.
4. The pharmaceutical composition according to any one of 1 to 3 above, wherein the HGF protein is a recombinant HGF protein.
5. The pharmaceutical composition according to any one of 1 to 4 above, wherein the HGF protein is a polypeptide that is any one of the following:
    (a) a polypeptide comprising the amino acid sequence shown in SEQ ID NO: 2;
    (b) a polypeptide comprising an amino acid sequence shown in SEQ ID NO: 2 in which one to several amino acids are deleted, substituted, or added; or
    (c) a polypeptide comprising an amino acid sequence having at least 90% identity with the amino acid sequence shown in SEQ ID NO: 2.
6. The pharmaceutical composition according to any one of 1 to 5 above, wherein the esophageal stenosis is caused by esophageal ulcer.
7. The pharmaceutical composition according to any one of 1 to 6 above, wherein esophageal ulcer is treated.
8. A stent comprising the pharmaceutical composition according to any one of 1 to 7 above.

This description includes part or all of the contents as disclosed in the specification and/or drawings of Japanese Patent Application No. 2014-164429, to which the present application claims priority.

Advantageous Effects of Invention

The composition of the present invention has effects of improving and/or preventing esophagus stenosis. Therefore, the composition of the present invention is particularly effective for treatment of esophageal stenosis caused by endoscopic submucosal dissection.

DESCRIPTION OF EMBODIMENTS

Figure 1:
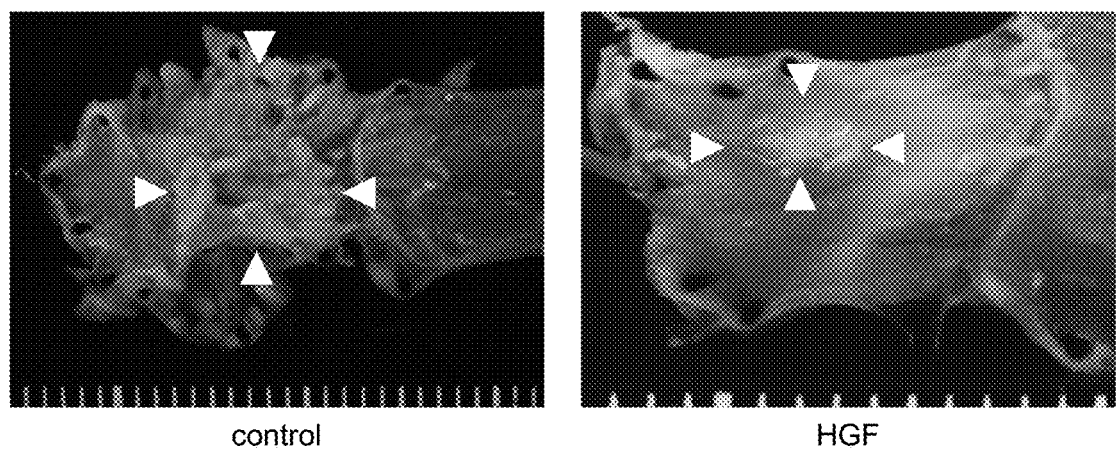
FIG. 1 shows the influence of intraperitoneal administration of recombinant human HGF on esophageal ulcer (indicated by arrow heads). "Control" shows case(s) in which human HGF was not administered.

The present invention relates to a pharmaceutical composition for treating and/or preventing esophageal stenosis, comprising a hepatocyte growth factor (HGF) protein as an active ingredient.

As described above, HGF is known as a growth factor that strongly promotes liver regeneration and also known as an important repair factor for damaged gastrointestinal mucosa. According to the present invention, the term "HGF" refers to mammal HGF, including human HGF.

The HGF protein can be prepared using a method known to those skilled in the art. For example, the HGF protein can be obtained by culturing primary culture cells or cells of an established cell line capable of promoting the HGF protein, separating the protein from a culture supernatant, and, if needed, purifying the protein.

Alternatively, the HGF protein can be produced/purified by a genetic engineering technique known to those skilled in the art. For example, it is possible to incorporate DNA that encodes the HGF protein or a fragment thereof into a suitable vector, introduce the vector into suitable host cells, and allow the protein to be expressed as a recombinant. Gene recombinant technology can be conducted in accordance with methods known in the art (e.g., Sambrook et al., "Molecular Cloning, A Laboratory Manual," Cold Spring Harbor Laboratory Press, 1989) unless otherwise specified.

The gene sequence and the amino acid sequence of HGF can be obtained by any method known in the art, for example, from public databases (e.g., NCBI (the U.S.), DDBJ (Japan), and EMBL (Europe)). It is possible to produce the HGF protein based on the sequence information registered in databases (GenBank accession no. M29145; cDNA sequence: SEQ ID NO: 1; amino acid sequence: SEQ ID NO: 2) by a method known in the art (e.g., gene recombination). Therefore, the HGF protein used in the present invention may be a recombinant HGF protein. In addition, the HGF protein used in the present invention may be a commercially available HGF protein. Examples of a commercially available HGF protein include recombinant human HGF expressed in CHO cells sold by SIGMA-Aldrich.

Examples of a vector used for production of a recombinant protein include plasmid vectors and viral vectors. Examples of viral vectors include Sendai virus, adenovirus, adeno-associated virus, retrovirus, and lentivirus. The vector may contain, for example, a promoter, an enhancer, a ribosome-binding site, a terminator, and, if needed, a selection marker, in addition to DNA to be expressed.

Examples of host cells include cells of known microorganisms (e.g., E. coli or yeast) and known culture cells such as animal cells (e.g., CHO cells, HEK-293 cells, and COS cells) and insect cells (e.g., BmN4 cells and SF9 cells) used in general.

It is possible to purify an expressed polypeptide from a culture supernatant of host cells by one or more of known methods of protein or polypeptide purification such as ammonium sulfate fractionation, separation by precipitation using an organic solvent (e.g., ethanol, methanol, or acetone), methods involving chromatography such as ion-exchange chromatography, isoelectric chromatography, gel filtration chromatography, hydrophobic chromatography, adsorption column chromatography, affinity chromatography using a substrate, antibody, or the like, reversed-phase chromatography, or HPLC, and filtration processes such as microfiltration, ultrafiltration, and reverse osmosis filtration.

HGF used in the present invention is not limited to a polypeptide comprising the amino acid sequence of SEQ ID NO: 2. It may be a polypeptide comprising an amino acid sequence shown in SEQ ID NO: 2 in which one to several amino acid residues are deleted, substituted, or added, as long as it has the ability to inhibit esophageal stenosis. Here, the range of "one to several" amino acids is not particularly limited; however, it is, for example, 1 to 10 amino acids, preferably 1 to 7 amino acids, more preferably 1 to 5 amino acids, and particularly preferably 1 to 3 or 1 to 2 amino acids.

In addition, HGF used in the present invention may be a polypeptide comprising an amino acid sequence having at least 70%, preferably at least 80%, more preferably at least 90%, and most preferably at least 95% (e.g., 97%, 98%, or 99%) identity with the amino acid sequence shown in SEQ ID NO: 2, as long as it has the ability to inhibit esophageal stenosis. The values for such identity are calculated by default using software (e.g., FASTA, DANASYS, or BLAST) for computing amino acid sequence identity.

Further, a protein fragment of HGF may be used as long as it has the ability to inhibit esophageal stenosis. Such protein fragment can be easily produced by preparing an arbitrary polypeptide based on the above nucleotide sequence and confirming whether the polypeptide has the ability to inhibit esophageal stenosis.

In a preferred embodiment of the present invention, the HGF protein is a polypeptide that is any one of the following: (a) a polypeptide comprising the amino acid sequence shown in SEQ ID NO: 2; (b) a polypeptide comprising the amino acid sequence shown in SEQ ID NO: 2 in which one to several amino acids are deleted, substituted, or added; or (c) a polypeptide comprising an amino acid sequence having at least 90% identity with the amino acid sequence shown in SEQ ID NO: 2. In addition, the HGF protein may undergo post-translational modification such as glycosylation or pyroglutamylation or modification with a water-soluble polymer (e.g., polyethylene glycol).

According to the present invention, the origin of the HGF protein is not limited. Specifically, examples of the HGF protein include mammal HGFs such as human HGF, mouse HGF (GenBank accession no. NM_010427.4; cDNA sequence: SEQ ID NO: 3; amino acid sequence: SEQ ID NO: 4), rat HGF (GenBank accession no. NM_017017.2; cDNA sequence: SEQ ID NO: 5; amino acid sequence: SEQ ID NO: 6), feline HGF (GenBank accession no. AB080187.1; cDNA sequence: SEQ ID NO: 7; amino acid sequence: SEQ ID NO: 8), canine HGF (GenBank accession no. AB090353.1; cDNA sequence: SEQ ID NO: 9; amino acid sequence: SEQ ID NO: 10), and bovine HGF (GenBank accession no. AB110822.1; cDNA sequence: SEQ ID NO: 11; amino acid sequence: SEQ ID NO: 12). The origin of HGF can be arbitrarily selected depending on a species of interest. For example, when the present invention is applied to humans, it is preferable to use human HGF. In general, the HGF protein is synthesized as a single-stranded precursor comprising a heavy chain and a light chain and then processed and glycosylated to result in mature HGF. Human HGF has a heavy chain comprising 463 amino acids and a light chain comprising 234 amino acids (Hirohito Tsubouchi and Yasushi Daikuhara, Protein, Nucleic Acid and Enzyme, Vol. 37, No. 12, 1992, pp. 2135-2143).

The term "esophageal stenosis" used herein means a state in which the esophageal lumen becomes narrowed, making it difficult to allow passage of foods, beverages, and the like.

The expression "esophageal stenosis occurring after endoscopic submucosal dissection" used herein means a state in which esophageal mucosa removed by endoscopic means is replaced by fibrous tissue, resulting in stenosis. Esophageal stenosis in the present invention may result from endoscopic submucosal dissection (ESD) for cases of early esophageal cancer (i.e., superficial esophageal cancer).

The pharmaceutical composition of the present invention can be administered via oral or parenteral administration (e.g., intravenous, intramuscular, subcutaneous, intraperitoneal, rectal, or transmucosal administration). In addition, the pharmaceutical composition of the present invention may be prepared in a suitable dosage form suitable depending on the route of administration. Specifically, it may be prepared in various pharmaceutical forms such as granules, tablets, pills, capsules, syrups, emulsions, suspensions, injectable agents for intravenous injection, arterial injection, or muscular injection, drops, topical agents, and suppositories.

The pharmaceutical composition of the present invention may be administered using a stent containing the pharmaceutical composition. Such stent may be, for example, a stent that can be endoscopically placed (i.e., an absorbable or detachable stent), and HGF contained as an active ingredient may be eluted or sustainably released from the stent. Therefore, one embodiment of the present invention relates to such stent.

The administration method and the dosage form can be appropriately selected depending on patient's sex, age, weight, symptoms, and the like.

The pharmaceutical composition comprising the HGF protein as an active ingredient according to the present invention can be formulated in accordance with an ordinary method (see, for example, Remington's Pharmaceutical Science, latest edition, Mark Publishing Company, and Easton, the U.S.), and the composition may contain a pharmaceutically acceptable carrier or an additive.

Examples of such carrier or pharmaceutical additive include water, pharmaceutically acceptable organic solvents, collagen, polyvinyl alcohol, polyvinyl pyrrolidone, carboxyvinyl polymer, sodium carboxymethyl cellulose, sodium polyacrylate, sodium alginate, water-soluble dextran, sodium carboxymethyl starch, pectin, methyl cellulose, ethyl cellulose, xanthan gum, gum arabic, casein, agar, polyethylene glycol, diglycerin, glycerin, propylene glycol, petrolatum, paraffin, stearyl alcohol, stearic acid, human serum albumin (HSA), mannitol, sorbitol, lactose, and surfactants serving as pharmaceutically acceptable additives.

In practical use, additives are selected from, but are not limited to, the above examples alone or in combination in accordance with the dosage form of the pharmaceutical composition of the present invention. For example, when the pharmaceutical composition is used as an injectable formulation, a purified HGF protein is dissolved in a solvent such as physiological saline, a buffer, or a glucose solution and mixed with a vessel adsorption inhibitor such as Tween 80, Tween 20, gelatin, or human serum albumin. The thus obtained mixture can be used. Alternatively, the pharmaceutical composition may be lyophilized to result in a dosage form that can be dissolved or reconstructed before use. Examples of a stabilizer that can be used for lyophilization include sugars and sugar alcohols such as mannitol and glucose.

The effective dosage of the therapeutic agent of the present invention is determined within a range of, for example, 0.001 mg to 1000 mg per 1 kg of body weight for single administration. However, the dosage of the pharmaceutical composition comprising the HGF protein according to the present invention is not limited thereto and thus can be appropriately selected depending on the patient's sex, age, weight, symptoms, and the like.

The target disease for which the therapeutic agent of the present invention is administered is esophageal stenosis, and in particular, esophageal stenosis occurring after endoscopic submucosal dissection. The disease may include esophageal stenosis secondary to or associated with different disease(s).

The timing of administering the therapeutic agent of the present invention may be either before or after the onset of clinical symptoms of the above disease, and the administration may be for the purpose of prevention or maintenance.

The present invention is described in more detail with reference to the Examples below. However, the scope of the present invention is not limited to the Examples.

EXAMPLES

Example 1: Influence of Recombinant Human HGF on Esophageal Ulcer

Figure 2:
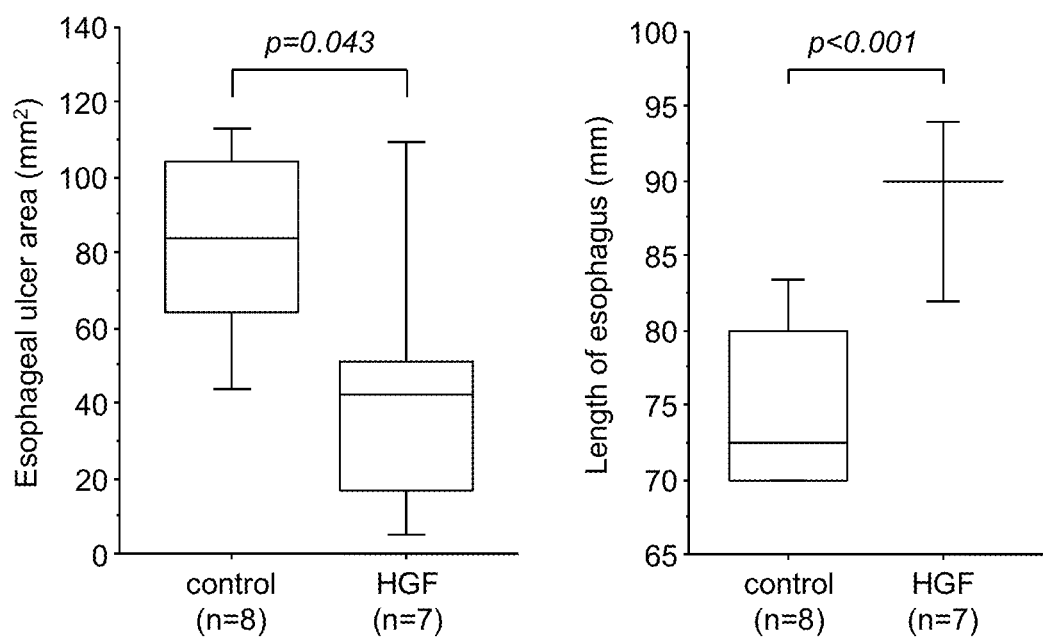
FIG. 2 shows the influence of intraperitoneal administration of recombinant human HGF on the esophageal ulcer area and the length of esophagus. "Control" shows case(s) in which human HGF was not administered.
Figure 3:
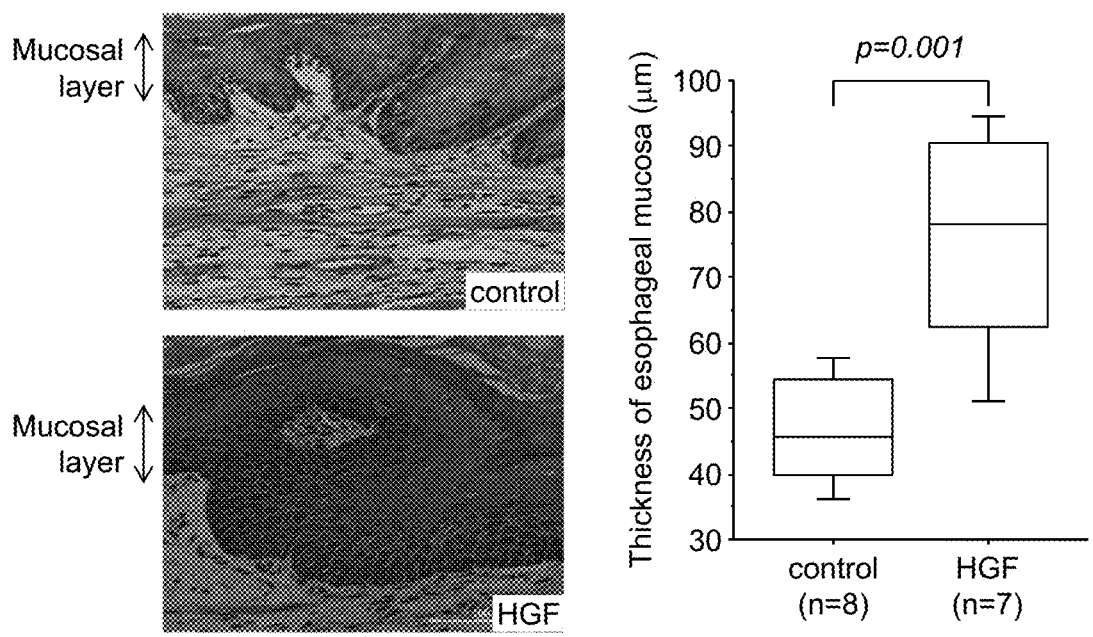
FIG. 3 shows the influence of intraperitoneal administration of recombinant human HGF on the mucosal layer of esophagus epithelium and the thickness of esophageal mucosa. "Control" shows case(s) in which human HGF was not administered.
Figure 4:
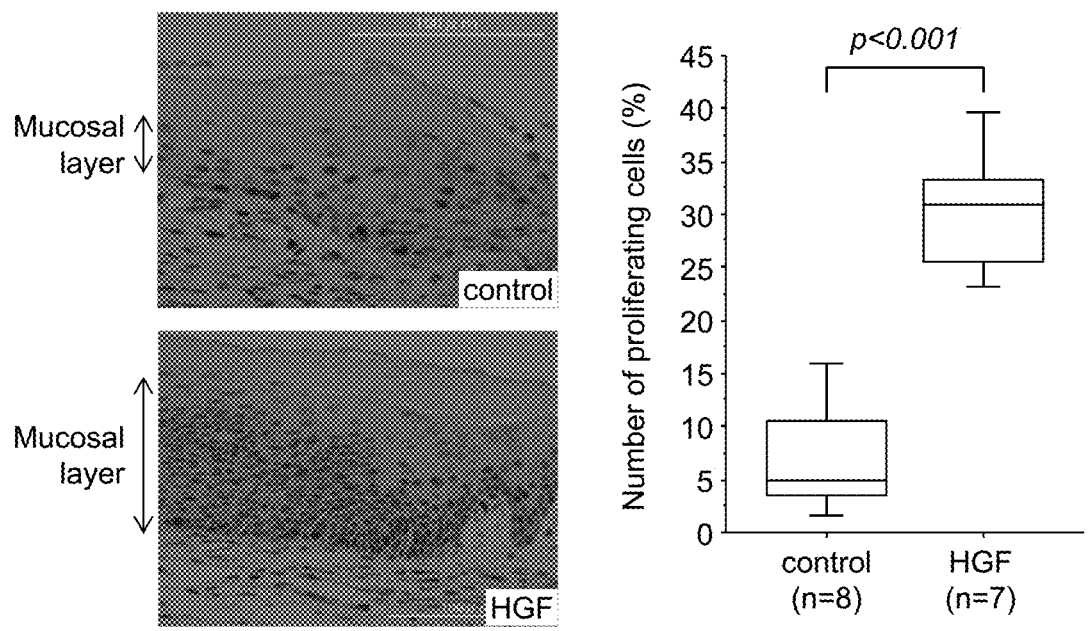
FIG. 4 shows the influence of intraperitoneal administration of recombinant human HGF on the mucosal layer of esophagus epithelium and proliferation of esophageal epithelial cells. "Control" shows case(s) in which human HGF was not administered.

Laparotomy was performed on 6-week-old SD rats. A single dose of 100% acetic acid (30 µg/rat) was injected into the subserosal layer of the lower esophagus so as to cause a mucosal defect of the esophagus. An osmotic pump containing a phosphate buffer solution (PBS) or recombinant human HGF (5 mg/ml) was placed in the abdominal cavity, followed by closing the abdomen. This osmotic pump continuously released the recombinant human HGF at a rate of 200 mg/day. The esophageal ulcer area and the length of the esophagus were examined 7 days after the administration of HGF. As a result, the recombinant human HGF significantly reduced the esophageal ulcer (FIG. 1 and the left image of FIG. 2) and remarkably inhibited the shortening of the esophagus (the right image of FIG. 2). In addition, the recombinant human HGF thickened the mucosa at the periphery of esophageal ulcer (FIG. 3) and significantly promoted the proliferation of the epithelial cells of the esophagus (FIG. 4).

Example 2: Influence of Recombinant Human HGF on Esophageal Stenosis

Laparotomy was performed on 6-week-old SD rats. A single dose of 100% acetic acid (30 µg/rat) was injected into the subserosal layer of the lower esophagus so as to cause a mucosal defect of the esophagus. An osmotic pump containing a phosphate buffer solution (PBS), recombinant human HGF (5 mg/ml), or methylprednisolone (250 mg/mL) was placed in the abdominal cavity, followed by closing the abdomen. The recombinant human HGF and methylprednisolone is continuously released at a rate of 200 mg/day and 10 mg/day, respectively, from this osmotic pump. The severity of esophageal stenosis was examined 7 days after the administration of recombinant HGF or methylprednisolone. In addition, the expression of Col1α1, TGF-β, TIMP1, and TIMP2 was analyzed using the method described below by real-time PCR.

Specifically, at first, total RNA was extracted using PureLink (registered trademark) RNA Mini Kits (Life technologies), and the concentration was determined using NanoDrop (Thermoscientific). RNase Free dH$_2$O was added as necessary so as to adjust the total RNA concentration of each sample to 200 ng/μl. Subsequently, reverse transcription was performed using 0.5 μg (500 ng) of total RNA as a template and random primers at 37° C. for 15 minutes for cDNA synthesis, followed by deactivation at 85° C. for 5 seconds. Next, real-time PCR was conducted using 0.0005 μg (0.5 ng) of cDNA as a template and primers listed in table 1 below at 40 cycles of 95° C. for 5 seconds and 60° C. for 34 seconds. Takara Ex Taq (registered trademark) (Takara Bio Inc.) was used as Taq polymerase.

[Table 1]

Figure 5:
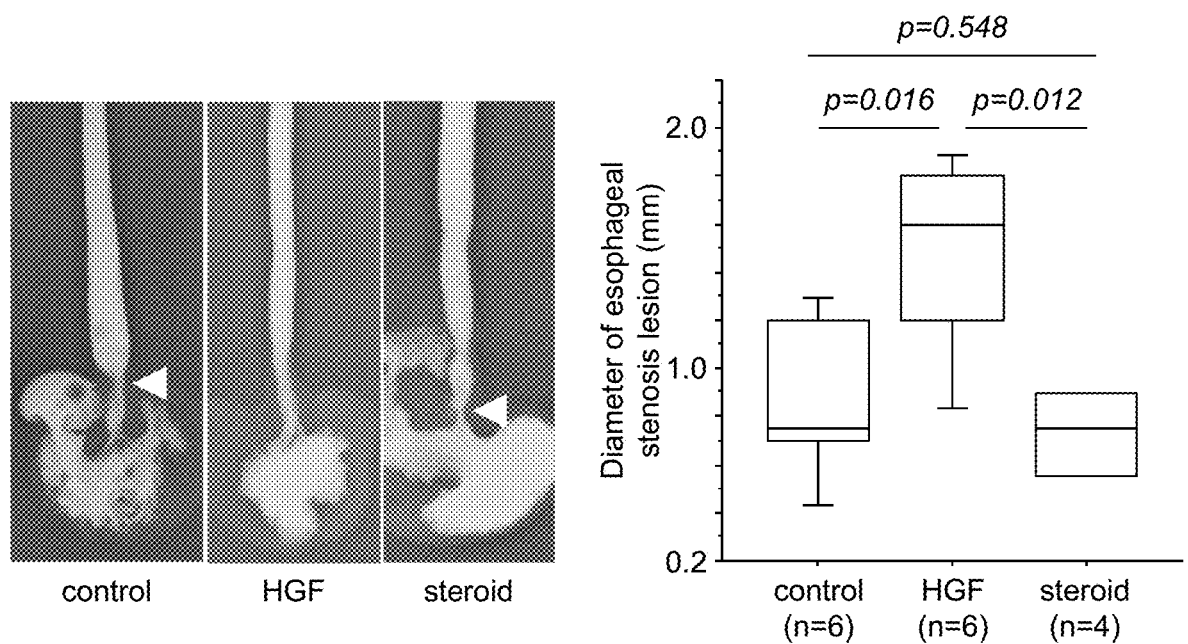
FIG. 5 shows the influence of intraperitoneal administration of recombinant human HGF or a steroid on the diameter of an esophageal stenosis lesion (indicated by each arrow). "Control" shows case(s) in which human HGF was not administered.
Figure 6:
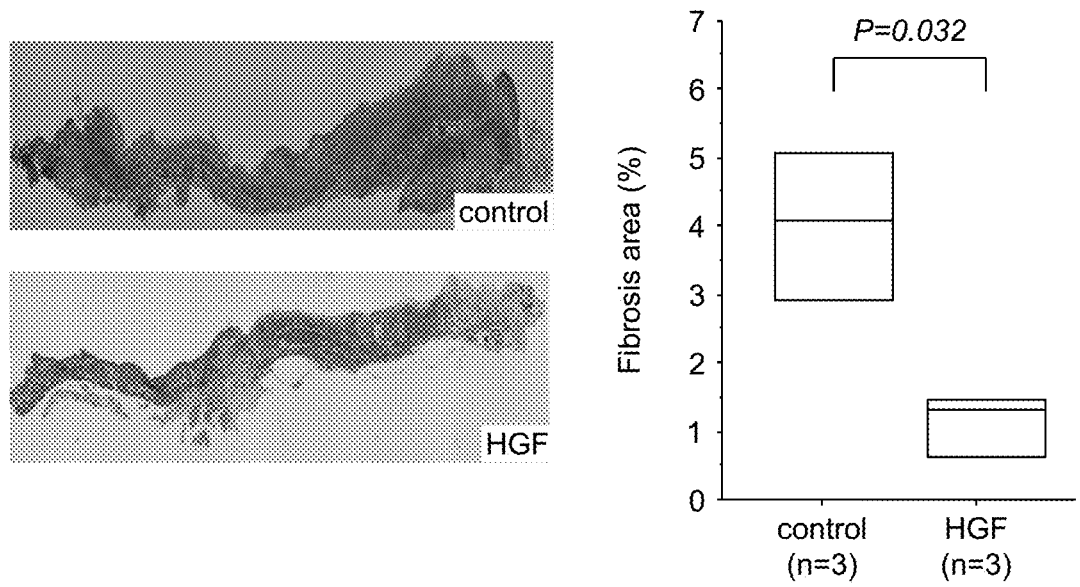
FIG. 6 shows the influence of intraperitoneal administration of recombinant human HGF on esophageal fibrosis. "Control" shows case(s) in which human HGF was not administered.
Figure 7:
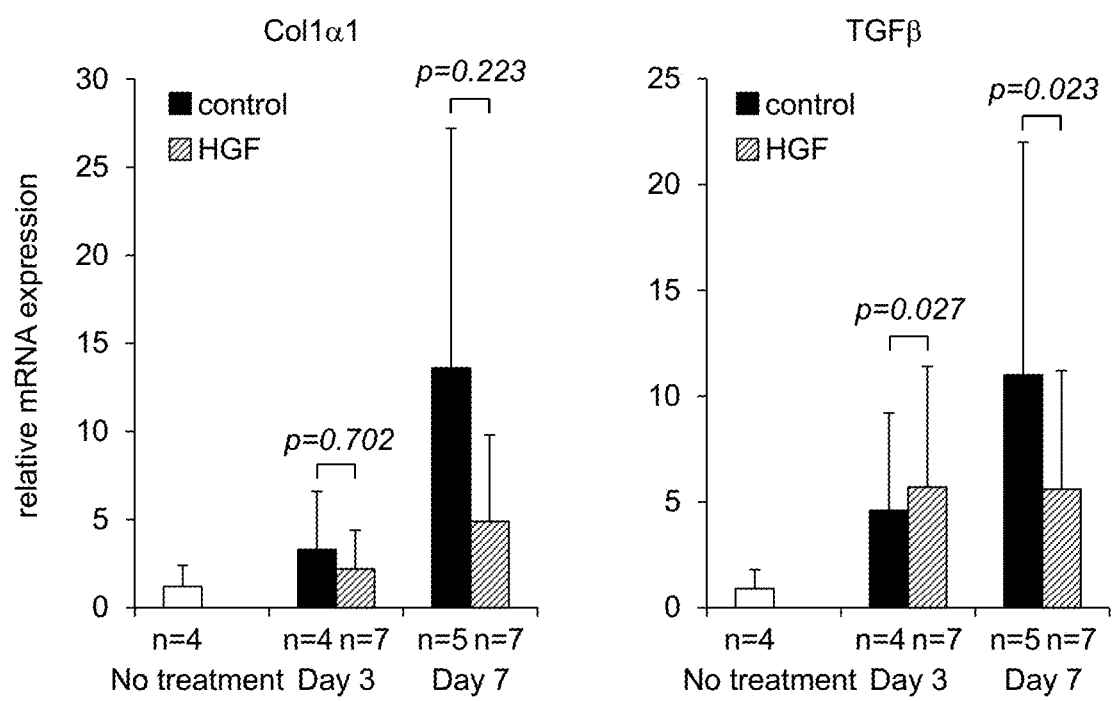
FIG. 7 shows the influence of intraperitoneal administration of recombinant human HGF on mRNA expression of col1α1 and TGF-β (on days 3 and 7). "Control" shows case(s) in which human HGF was not administered.
Figure 8:
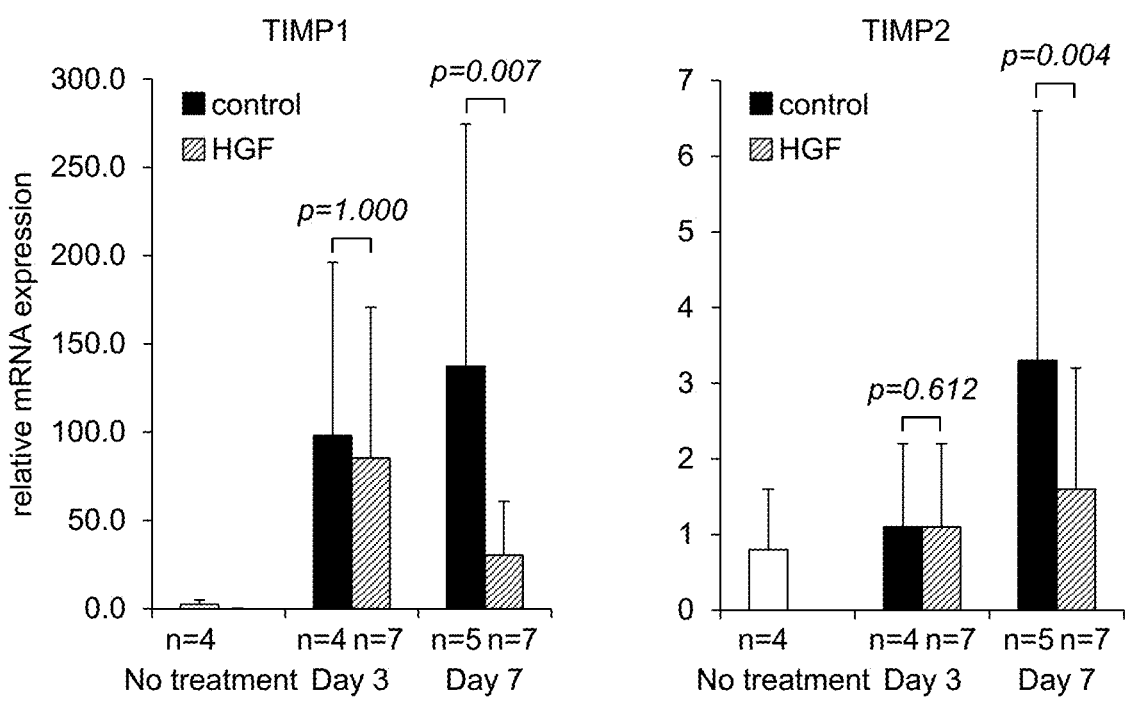
FIG. 8 shows the influence of intraperitoneal administration of recombinant human HGF on mRNA expression of TIMP1 and TIMP2 (on days 3 and 7). "Control" shows case(s) in which human HGF was not administered.

As a result, PBS and methylprednisolone (i.e., a steroid) did not influence esophageal stenosis, while recombinant human HGF significantly inhibited esophageal stenosis (FIG. 5). In addition, esophageal fibrosis was significantly inhibited by administrating HGF (FIG. 6), and the expression of the fibrosis-related molecules (i.e., Col1α1, TGF-β, TIMP1, and TIMP2) was also inhibited (FIGS. 7 and 8).

The above results suggested that HGF has effects of inhibiting stenosis (shrinkage) so as to improve or prevent esophageal stenosis. Accordingly, it is considered that the composition comprising HGF as an active ingredient according to the present invention is particularly effective for treatment and/or prevention of stenosis of the esophagus with a mucosal deficit caused by endoscopic submucosal dissection.

INDUSTRIAL APPLICABILITY

The composition of the present invention has effects of improving and/or preventing esophageal stenosis. Therefore, the composition of the present invention is particularly effective for treatment and/or prevention of esophageal stenosis occurring after endoscopic submucosal dissection.
Sequence Listing Free Text
Primers: SEQ ID NO: 13 to 22
All publications, patents, and patent applications cited herein are incorporated herein by reference in their entirety.

The invention claimed is:

1. A method for inhibiting esophageal stenosis in a patient having an esophageal ulcer, comprising administering to the patient a pharmaceutical composition comprising hepatocyte growth factor (HGF) protein in a dosage effective to inhibit esophageal stenosis.

2. The method according to claim 1, wherein the HGF protein is a human HGF protein.

3. The method according to claim 1, wherein the HGF protein is a recombinant HGF protein.

4. The method according to claim 1, wherein the HGF protein is a polypeptide that is any one of the following:
   (a) a polypeptide comprising the amino acid sequence shown in SEQ ID NO: 2;
   (b) a polypeptide comprising an amino acid sequence shown in SEQ ID NO: 2 in which one to several amino acids are deleted, substituted, or added; or
   (c) a polypeptide comprising an amino acid sequence having at least 90% identity with the amino acid sequence shown in SEQ ID NO: 2.

5. The method according to claim 1, wherein the pharmaceutical composition is administered using a stent.

6. The method according to claim 1, wherein the pharmaceutical composition comprises a pharmaceutical additive selected from the group consisting of water, a pharmaceutically acceptable organic solvent, collagen, polyvinyl alcohol, polyvinyl pyrrolidone, carboxyvinyl polymer, sodium carboxymethyl cellulose, sodium polyacrylate, sodium alginate, water-soluble dextran, sodium carboxymethyl starch, pectin, methyl cellulose, ethyl cellulose, xanthan gum, gum arabic, casein, agar, polyethylene glycol, diglycerin, glycerin, propylene glycol, petrolatum, paraffin, stearyl alcohol, stearic acid, human serum albumin (HSA), mannitol, sorbitol, lactose, and a surfactant.

7. A method for inhibiting esophageal stenosis in a patient that has undergone endoscopic submucosal dissection, comprising administering to the patient a pharmaceutical composition comprising hepatocyte growth factor (HGF) protein in a dosage effective to inhibit esophageal stenosis.

8. The method according to claim 7, wherein the HGF protein is a human HGF protein.

9. The method according to claim 7, wherein the HGF protein is a recombinant HGF protein.

10. The method according to claim 7, wherein the HGF protein is a polypeptide that is any one of the following:
    (a) a polypeptide comprising the amino acid sequence shown in SEQ ID NO: 2;
    (b) a polypeptide comprising an amino acid sequence shown in SEQ ID NO: 2 in which one to several amino acids are deleted, substituted, or added; or
    (c) a polypeptide comprising an amino acid sequence having at least 90% identity with the amino acid sequence shown in SEQ ID NO: 2.

11. The method according to claim 7, wherein the pharmaceutical composition is administered using a stent.

12. The method according to claim 7, wherein the pharmaceutical composition comprises a pharmaceutical additive selected from the group consisting of water, a pharmaceutically acceptable organic solvent, collagen, polyvinyl alcohol, polyvinyl pyrrolidone, carboxyvinyl polymer, sodium carboxymethyl cellulose, sodium polyacrylate, sodium alginate, water-soluble dextran, sodium carboxymethyl starch, pectin, methyl cellulose, ethyl cellulose, xanthan gum, gum arabic, casein, agar, polyethylene glycol, diglycerin, glycerin, propylene glycol, petrolatum, paraffin, stearyl alcohol, stearic acid, human serum albumin (HSA), mannitol, sorbitol, lactose, and a surfactant.

* * * * *